United States Patent
Howell et al.

(10) Patent No.: US 10,227,804 B2
(45) Date of Patent: Mar. 12, 2019

(54) DEPLOYABLE JOINT

(71) Applicant: BRIGHAM YOUNG UNIVERSITY, Provo, UT (US)

(72) Inventors: Larry L. Howell, Orem, UT (US); Todd Nelson, Provo, UT (US)

(73) Assignee: Brigham Young University, Provo, UT (US)

( * ) Notice: Subject to any disclaimer, the term of this patent is extended or adjusted under 35 U.S.C. 154(b) by 200 days.

(21) Appl. No.: 14/969,979

(22) Filed: Dec. 15, 2015

(65) Prior Publication Data
US 2016/0177605 A1    Jun. 23, 2016

Related U.S. Application Data

(60) Provisional application No. 62/124,405, filed on Dec. 17, 2014.

(51) Int. Cl.
*E05D 1/04* (2006.01)
*E05D 1/00* (2006.01)
(Continued)

(52) U.S. Cl.
CPC ............... *E05D 1/04* (2013.01); *E05D 1/00* (2013.01); *F16C 11/04* (2013.01); *A61F 2/30* (2013.01);
(Continued)

(58) Field of Classification Search
CPC .. A61F 2002/30693; A61F 2002/30484; A61F 2/4425; A61F 2002/30092; A61F 2/30; E05D 1/04
See application file for complete search history.

(56) References Cited

U.S. PATENT DOCUMENTS 3,488,098 A    1/1970  Sobczak
3,730,007 A    5/1973  Wellington
(Continued)

OTHER PUBLICATIONS

International Search Report and Written Opinion received for PCT Patent Application No. PCT/US2015/066016, dated Feb. 16, 2016, 12 pages.
(Continued)

*Primary Examiner* — Bruce E Snow
*Assistant Examiner* — Melissa Hoban
(74) *Attorney, Agent, or Firm* — Brake Hughes Bellermann LLP

(57) ABSTRACT

According to an aspect, a device may include a deployable rolling joint having a first deployable joint member, a second deployable joint member, and a plurality of flexures coupled to the first deployable joint member and the second deployable joint member. The deployable rolling joint may move from an undeployed state to a deployed state in which the first deployable joint member forms a convex surface portion and the second deployable joint member forms a convex surface portion. When the deployable rolling joint is in the deployed state, the convex surface portion of the first deployable joint member may roll with respect the convex surface portion of the second deployable joint member, and the plurality of flexures may hold the first deployable joint member and the second deployable joint member together as the first deployable joint member and the second deployable joint member roll across each other.

20 Claims, 14 Drawing Sheets

(51) Int. Cl.
*F16C 11/04* (2006.01)
*A61F 2/30* (2006.01)

(52) U.S. Cl.
CPC . *A61F 2002/30092* (2013.01); *E05Y 2800/00* (2013.01); *E05Y 2900/502* (2013.01); *E05Y 2900/60* (2013.01)

(56) References Cited

U.S. PATENT DOCUMENTS

| | | | |
|---|---|---|---|
| 3,850,043 A | 11/1974 | Tarbox | |
| 3,927,438 A | 12/1975 | Blake | |
| 3,932,045 A | 1/1976 | Hillberry et al. | |
| 3,945,053 A | 3/1976 | Hillberry et al. | |
| 4,163,303 A | 8/1979 | Hanna | |
| 4,267,608 A * | 5/1981 | Bora, Jr. | A61F 2/3836 403/111 |
| 4,558,911 A | 12/1985 | Ruoff | |
| 4,973,291 A | 11/1990 | Mottate | |
| 5,086,541 A | 2/1992 | Auternaud et al. | |
| 7,328,481 B2 | 2/2008 | Barnett | |
| 7,354,033 B1 | 4/2008 | Murphey et al. | |
| 7,515,385 B1 | 4/2009 | Abrahamson et al. | |
| 8,308,801 B2 | 11/2012 | Halverson et al. | |
| 2004/0024462 A1* | 2/2004 | Ferree | A61F 2/4425 623/17.14 |
| 2007/0191958 A1* | 8/2007 | Abdou | A61B 17/025 623/17.16 |
| 2011/0196476 A1* | 8/2011 | Forsell | A61F 2/2421 623/1.24 |
| 2012/0109134 A1* | 5/2012 | Forsell | A61F 2/3603 606/80 |
| 2014/0238876 A1 | 8/2014 | Chen et al. | |

OTHER PUBLICATIONS

Messenger, Robert K., "Integrated Piezoresistive Sensing for Feedback Control of Compliant MEMS", Brigham Young University, Oct. 12, 2007, 90 pages.

* cited by examiner

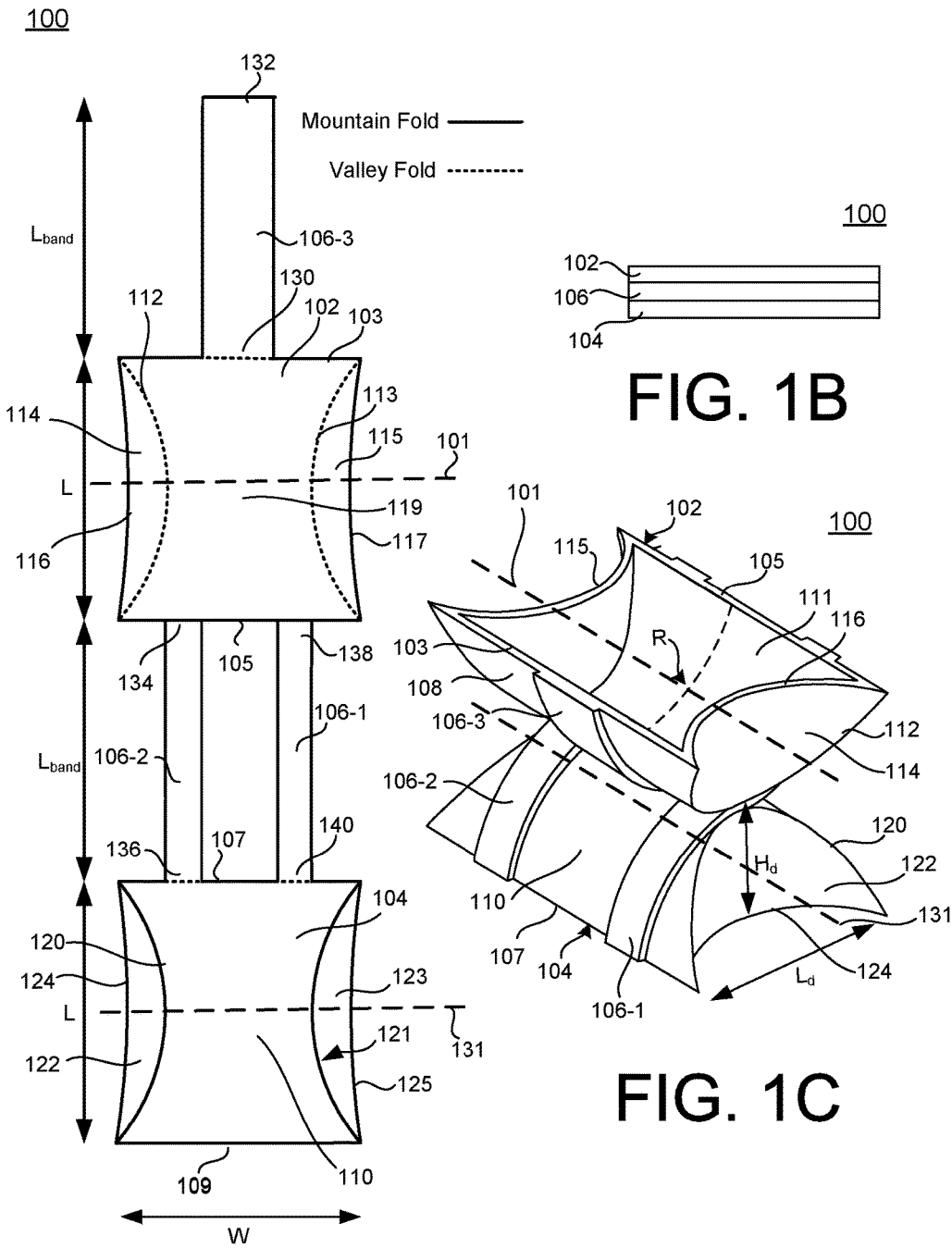

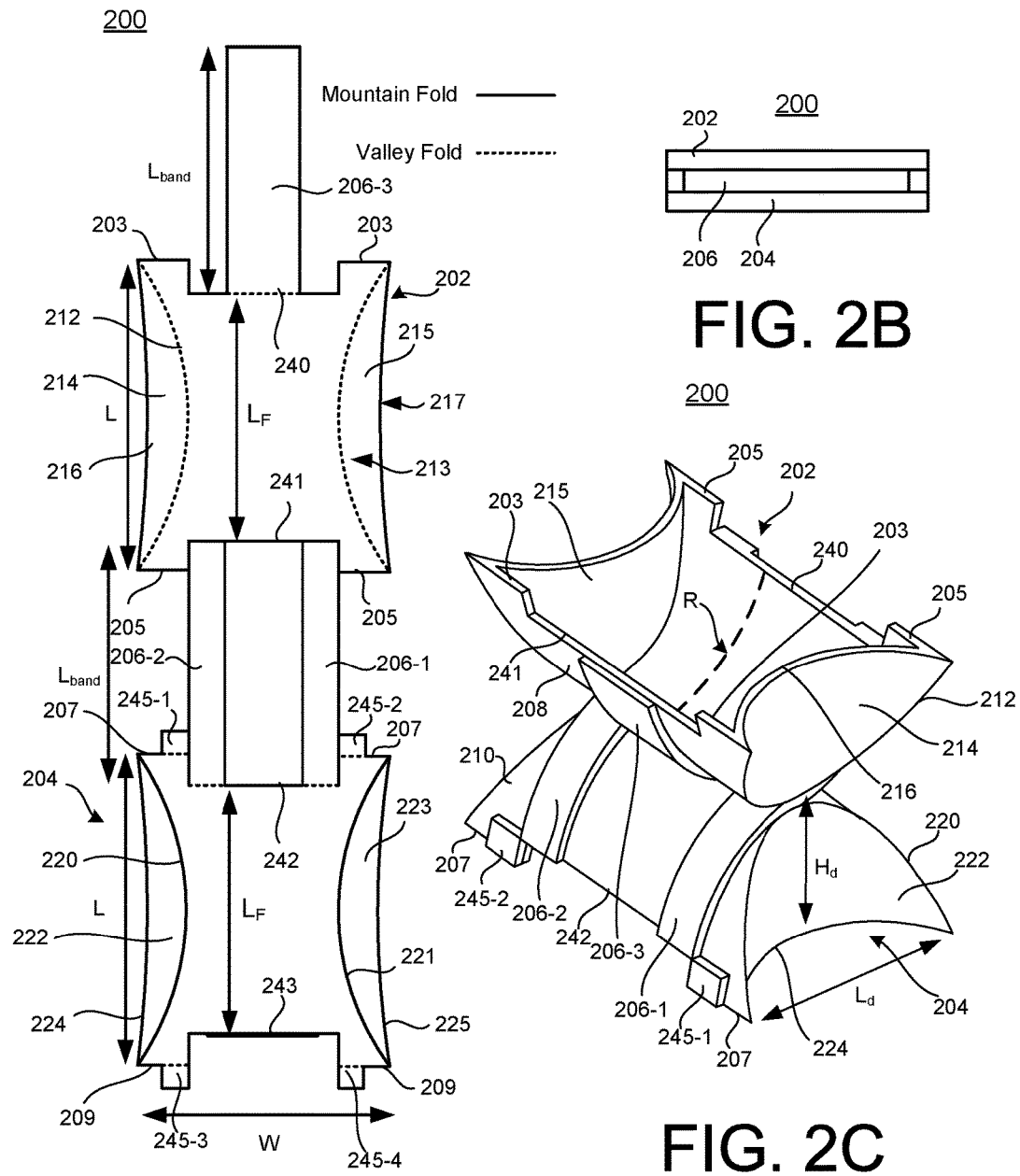

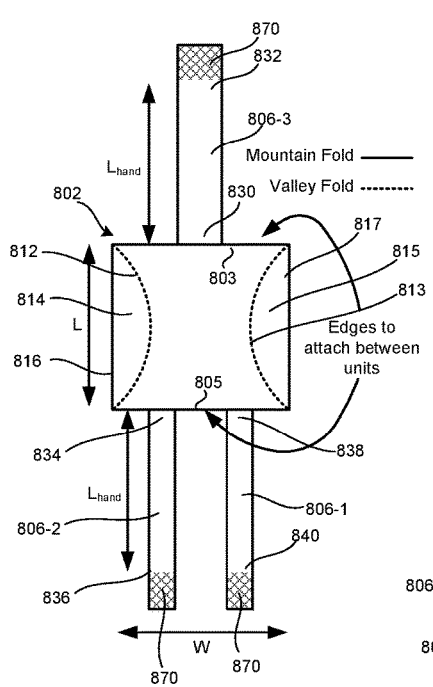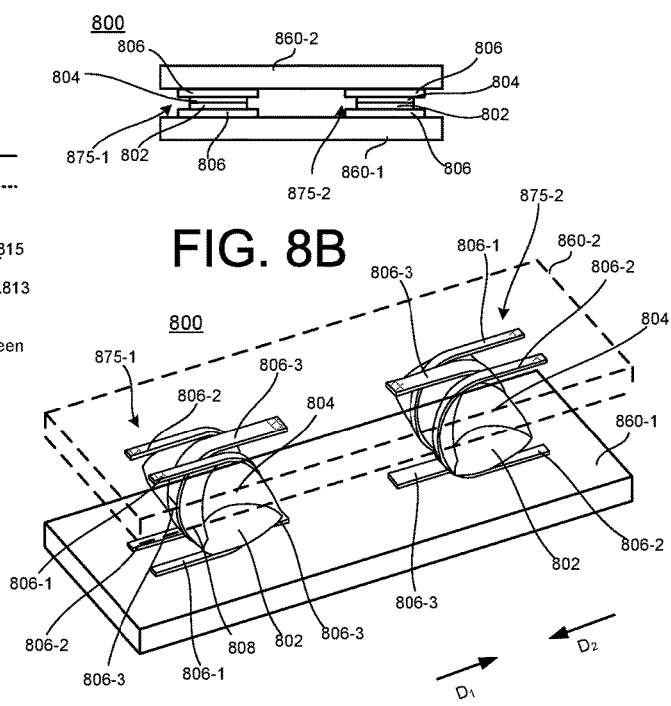
FIG. 8A
FIG. 8B
FIG. 8C

DEPLOYABLE JOINT

CROSS-REFERENCE TO RELATED APPLICATION

This application is a Non-provisional of, and claims priority to, U.S. Patent Application No. 62/124,405, filed on Dec. 17, 2015, entitled "DEPLOYABLE COMPLIANT ROLLING-CONTACT ELEMENT (D-CORE) WITH CAPABILITIES TO BE STOWED IN A FLAT POSITION AND DEPLOYED TO A FUNCTIONAL POSITION AS WELL AS A DEPLOYABLE TRANSLATING PLATFORM DERIVED FROM JOINT", which is incorporated by reference herein in its entirety.

STATEMENT REGARDING FEDERALLY SPONSORED RESEARCH

This invention was made with government support under a grant awarded by National Science Foundation and the Air Force Office of Scientific Research, Contract No. EFRI-ODISSEI-1240417.

TECHNICAL FIELD

This disclosure relates generally to a deployable joint.

BACKGROUND

Rolling joint hinges are used in a wide variety of applications. In some examples, a rolling joint hinge may use a mechanism between two rollers to create linear displacement. In some cases, the size of the rolling joint hinge may be too large for space-constrained applications. Also, the cost of manufacturing conventional hinges may be relatively high because the individual components may need to be separately created and then assembled. Thus, a need exists for devices and methods address the shortfalls of present technology and to provide other new and innovative features.

SUMMARY

According to an aspect, a device may include a deployable rolling joint having a first deployable joint member, a second deployable joint member, and a plurality of flexures coupled to the first deployable joint member and the second deployable joint member. The deployable rolling joint is configured to move from an undeployed state to a deployed state in which the first deployable joint member forms a convex surface portion and the second deployable joint member forms a convex surface portion. When the deployable rolling joint is in the deployed state, the convex surface portion of the first deployable joint member is configured to roll with respect the convex surface portion of the second deployable joint member, and the plurality of flexures is configured to hold the first deployable joint member and the second deployable joint member together as the first deployable joint member and the second deployable joint member roll across each other.

In some examples, the device may include one or more of the following features (or any combination thereof). When the deployable rolling joint is in the undeployed state, the first deployable joint member and the second deployable joint member may be devoid of a convex surface portion. When the deployable rolling joint is in the undeployed state, the first deployable joint member may be disposed on the second deployable joint with the plurality of flexures disposed between the first deployable joint member and the second deployable joint member. The first deployable joint member, the second deployable joint member, and the plurality of flexures may be integrally formed from a single, continuous sheet of material. Each of the first deployable joint member and the second deployable joint member may include a first curved crease forming a first foldable portion, and a second curved crease forming a second foldable portion, where the first foldable portion and the second foldable portion is configured to bend toward each other via the first curved crease and the second curved crease. The first deployable joint member may include a memory shape material, where the memory shape material biases the first deployable joint member to the deployed state. The device may be a medical device having a first portion and a second portion, where the first deployable joint member is coupled to the first portion of the medical device, and the second deployable joint member is coupled to the second portion of the medical device. The medical device may be configured to be inserted into a body of a patient.

According to another aspect, an apparatus may include a deployable joint member having a layer of material, and a plurality of flexures coupled to the deployable joint member. The deployable joint member may be configured to move from an undeployed state in which the layer of material is substantially flat to a deployed state in which the layer of material forms a convex surface portion.

In some examples, the apparatus may include any of the above or below features (or any combination thereof). The deployable joint member and the plurality of flexures may be integrally formed. The deployable joint member may include a first curved crease forming a first foldable portion, and a second curved crease forming a second foldable portion, where the first foldable portion and the second foldable portion is configured to move toward each other to form the convex surface portion. The deployable joint member may include a first lateral side and a second lateral side, and the deployable joint member may include a first end and a second end. The first foldable portion may extend between the first curved crease and the first end. The second foldable portion may extend between the second curved crease and the second end. The first end and/or the second end may include a curved portion. The plurality of flexures may include a first flexure, a second flexure, and a third flexure. The first flexure and the second flexure may extend from a first lateral side of the deployable joint member, and the third flexure may extend from a second lateral side of the deployable joint member, where the second lateral side is opposite to the first lateral side.

In some examples, the deployable joint member is a first deployable joint member, and the apparatus further includes a second deployable joint member having a layer of material, where the second deployable joint member is configured to move from an undeployed state in which the layer of material of the second deployable joint member is substantially flat to a deployed state in which the layer of material of the second deployable joint member forms a convex surface portion. The plurality of flexures may be coupled to the first deployable joint member and the second deployable joint member. When the first deployable joint member and the second deployable joint member are in the deployed state, the convex surface portion of the first deployable joint member may be configured to roll with respect the convex surface portion of the second deployable joint member. The first deployable joint member, the second deployable joint member, and the plurality of flexures may be integrally formed.

In some examples, the deployable joint member is a first deployable joint member, and the plurality of flexures are a plurality of first flexures, the apparatus further includes a second deployable joint member having a layer of material and a plurality of second flexures coupled to the second deployable joint member. The second deployable joint member may be configured to move from an undeployed state in which the layer of material of the second deployable joint member is substantially flat to a deployed state in which the layer of material of the second deployable joint member forms a convex surface portion. The second deployable joint member may be coupled to the first deployable joint member. The apparatus may further include a first platform coupled to the plurality of first flexures, and a second platform coupled to the plurality of second flexures. The first deployable joint member and the second deployable joint member may be disposed between the first platform and the second platform, where, when the first and second deployable joint members are in the deployed state, the first platform is configured to translate with respect to the second platform.

According to another aspect, a device may include a first deployable joint member, a plurality of first flexures coupled to the first deployable joint member and a first platform, a second deployable joint member, and a plurality of second flexures coupled to the second deployable joint member and a second platform. The first deployable joint member and the second deployable joint member may be configured to move from an undeployed state to a deployed state in which the first deployable joint member forms a convex surface portion and the second deployable joint member forms a convex surface portion. When the first deployable joint member and the second deployable joint member are in the deployed state, the first platform may be configured to translate with respect to the second platform. In some examples, when the first deployable joint member and the second deployable joint member are in the undeployed state, the first deployable joint member and the second deployable joint member may be in a linear configuration.

BRIEF DESCRIPTION OF THE DRAWINGS

FIG. 1A illustrates a deployable rolling joint in a planar state according to an aspect.

FIG. 1B illustrates the deployable rolling joint in a compact, undeployed state according to an aspect.

FIG. 1C illustrates the deployable rolling joint in a deployed state according to an aspect.

FIG. 2A illustrates a deployable rolling joint in a planar state according to another aspect.

FIG. 2B illustrates the deployable rolling joint in a compact, undeployed state according to another aspect.

FIG. 2C illustrates the deployable rolling joint in a deployed state according to another aspect.

FIG. 8A illustrates a first deployable joint member in a planar state that is used in a deployable translating platform assembly according to an aspect.

FIG. 8B illustrates the deployable translating platform assembly in an assembled, but undeployed state according to an aspect.

FIG. 8C illustrates the deployable translating platform assembly in a deployed state according to an aspect.

DETAILED DESCRIPTION

The implementations discussed herein provide a deployable rolling joint that can be manufactured from a single sheet, folded into a flat, compact state, and then deployed into a device capable of hinge-like motion. In some examples, the deployable rolling joint may include two joint members that are connected by flexures to create a one-degree-of-freedom angular joint with a moving instantaneous axis of rotation. In some examples, the deployable rolling joint may move from a compact, undeployed state in which the joint members are relatively flat to a deployed state in which the joint members expand to form convex surface portions configured to roll with respect to each. For example, the convex surface portions are configured to face either such that they can roll with respect to other. The flexures are configured to hold the joint members together while enabling rotational movement. Also, the implementations discussed herein provide a deployable translating platform assembly by using two or more inverted joint members. For example, the joint members in the deployable translating platform assembly are connected to each other such that their convex surface portions face opposite to one another in the deployed state. The two or more joint members are coupled between platforms using flexures. Similar to the deployable rolling joint, the deployable translating platform assembly may move from a compact, undeployed state in which the joint members are in a relatively flat configuration (thus the platforms are relatively close to each other) to a deployed state in which the joint members expand to form convex surface portions (e.g., the convex surface portions face away from each other). In the deployed state, the platforms may linearly translate with respect to each other (e.g., the convex surface portions functioning as rollers between the platforms).

Figure 1D:
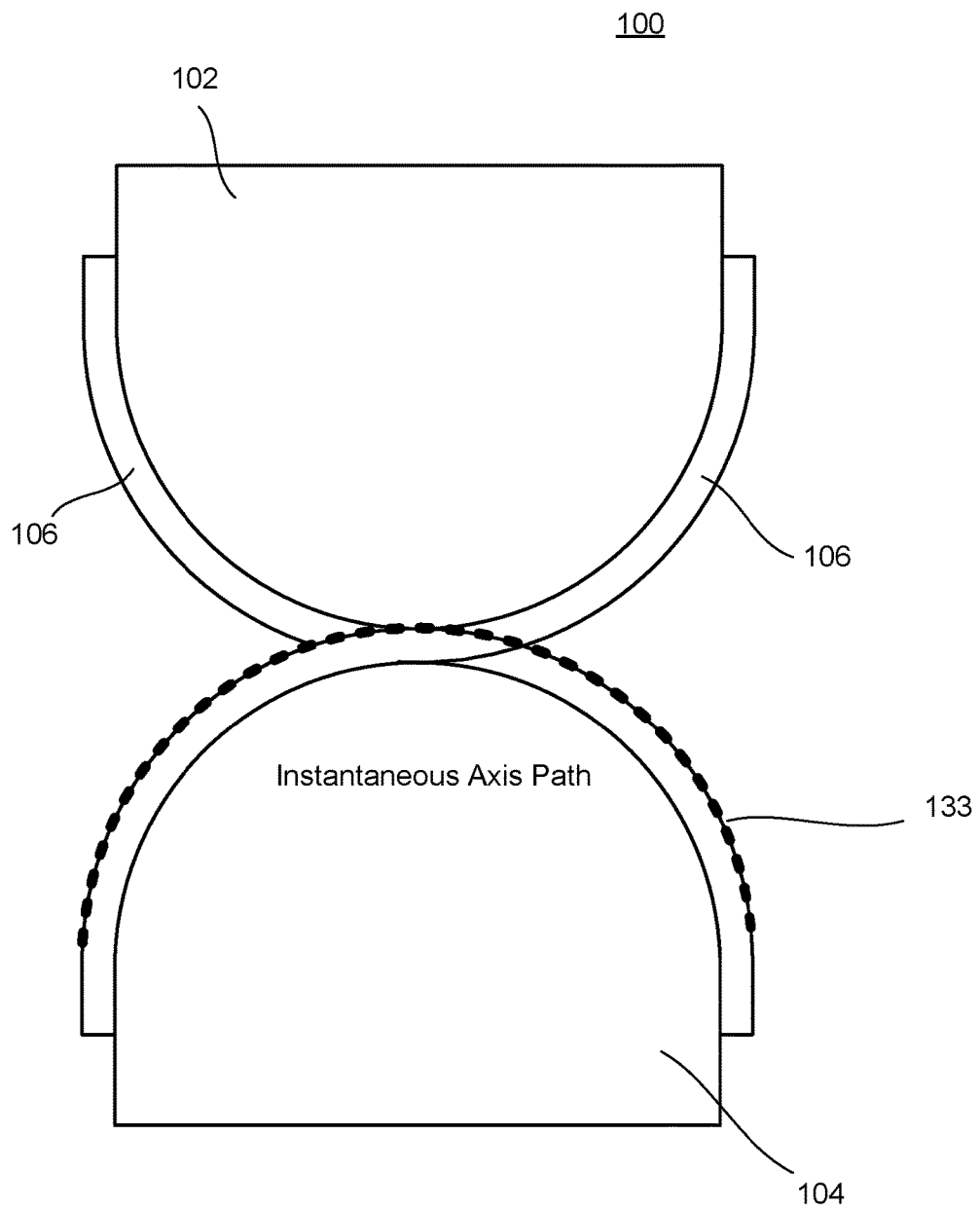
FIG. 1D illustrates an instantaneous axis path of the deployable rolling joint according to an aspect.

FIG. 1A illustrates a deployable rolling joint 100 in a planar state according to an aspect. FIG. 1B illustrates the deployable rolling joint 100 in a compact, undeployed state according to an aspect. FIG. 1C illustrates the deployable rolling joint 100 in a deployed state according to an aspect. FIG. 1D illustrates an instantaneous axis path 133 of the deployable rolling joint 100 according to an aspect. The deployable rolling joint 100 may include a first deployable joint member 102, a second deployable joint member 104, and a plurality of flexures 106 coupled to the first deployable joint member 102 and the second deployable joint member 104.

The first deployable joint member 102, the second deployable joint member 104, and the flexures 106 may be constructed from a sheet of material in a planar state. The type of material may widely vary depending on the application of the deployable rolling joint 100. In some examples, the sheet of material may include a metal-based material, a polymer-based material, or a combination of the metal-based material and the polymer-based material. In some examples, the sheet of material may be a single, continuous layer of material. The sheet of material may be cut to form the first deployable joint member 102, the second deployable joint member 104, and the flexures 106. As such, the first deployable joint member 102, the second deployable joint member 104, and the flexures 106 may be integrally or monolithically formed (e.g., included in a single continuous sheet). In some examples, because the deployable rolling joint 100 can be manufactured from a single sheet of material in the planar state, manufacturing costs associated with the deployable rolling joint 100 may be reduced as compared with conventional rolling joints. In other examples, the first deployable joint member 102, the second deployable joint member 104, and/or the flexures 106 are formed separately (e.g., two or more separate sheets of material) and then coupled together using any type of coupling mechanism (e.g. (e.g., heat-sealed, adhesive, interlocking coupling features, fasteners, etc.). In some examples, the first deployable joint member 102 and one or more flexures 106 may be formed from layer of material, and the second deployable joint member 104 and one or more flexures 106 may be formed from a separate layer of material, and the first deployable joint member 102 and the second deployable joint member 104 may be coupled together via the flexures 106.

The deployable rolling joint 100 of FIG. 1A may be folded to create the compact, undeployed state of FIG. 1B. For instance, the compact, undeployed state is a state in which the deployable rolling joint 100 is assembled, but not functionally deployed. The first deployable joint member 102 may be folded on top of the second deployable joint member 104 (or vice versa) in a manner that the flexures 106 extend over the rolling surfaces (convex surface portion 108, convex surface portion 110) of the first and second deployable joint members 102, 104. Also, it is noted that since FIG. 1A is a top view, FIG. 1A depicts the surface that forms the convex surface portion 110 for the second deployable joint member 104, whereas the surface that forms the concave surface portion 111 is depicted for the first deployable joint member 102 (e.g., in FIG. 1A, the first deployable joint member 102 may be "flipped" with respect to the second deployable joint member 104). In order to complete the assembly, a second end portion 132 of a third flexure 106-3 may be coupled to a second lateral side 109 of the second deployable joint member 104. The third flexure 106-3 is coupled to the second deployable joint member 104 using any type of coupling mechanism (e.g., heat-sealed, adhesive, interlocking coupling features, fasteners, etc.). In the compact, undeployed state of FIG. 1B, the deployable rolling joint 100 may include three layers positioned on top of each other (e.g., the first deployable joint member 102, the flexures 106, and the second deployable joint member 104).

The first deployable joint member 102 and the second deployable joint member 104 are relatively flat in the compact or stowed position. The first deployable joint member 102 and the second deployable joint member 104 may include curved creases (e.g., curved creases 112, 113, 120, 121), which allow the first deployable joint member 102 and the second deployable joint member 104 to expand into the deployed state of FIG. 1C, which form the convex surface portion 108 and the convex surface portion 110 in which the first deployable joint member 102 and the second deployable joint member 104 rotate with respect to each other. The flexures 106 are configured to hold the first and second deployable joint members 102, 104 together while allowing rotational movement.

In the deployed state, a longitudinal axis 101 of the first deployable joint member 102 may be aligned (e.g., disposed in the same plane) with a longitudinal axis 131 of the second deployable joint member 102. In other words, in the deployed state, the longitudinal axis 101 of the first deployable joint member 102 may extend in the same direction as the longitudinal axis 131 of the second deployable joint member 102. In other examples, the longitudinal axis 101 of the first deployable joint member 102 may be rotated or angled with respect to the longitudinal axis 131 of the second deployable joint member 102.

The deployable rolling joint 100 is deployable in the sense that it can transition from the compact, undeployed state in which the first and second deployable joint members 102, 104 are substantially flat to the deployed state in which the deployable rolling joint 100 can operate as a complaint rolling-contact element. In the deployed state of FIG. 1C, the first deployable joint member 102 may form the convex surface portion 108 and the second deployable joint member 104 may form the convex surface portion 110, where the convex surface portion 108 is configured to roll on the convex surface portion 110 (and vice versa), and the flexures 106 are configured to hold the first deployable joint member 102 and the second deployable joint member 104 together as the first deployable joint member 102 and the second deployable joint member 104 roll across each other. In some examples, the geometry of the curved creases (112, 113, 120, 121) to form the convex surface portion 108 and the convex surface portion 110, as well as the length ($L_{band}$) may determine the range of motion for the angular deflection of the deployable rolling joint 100 and the radius R of each of the first deployable joint member 102 and the second deployable joint member 104 in the deployed state. In some examples, referring to FIG. 1A, the length ($L_{band}$) of each flexure 106 may be equal to the length (L) of each of the first deployable joint member 102 and the second deployable joint member 104, which may provide the full range of rotational movement (e.g., 180 degrees). However, in some examples, the length ($L_{band}$) of one or more of the flexures 106 may be different (e.g., shorter) than the length (L) of the first deployable joint member 102 and/or the second deployable joint member 104 to provide a different range of movement.

The deployable rolling joint 100 may be embodied in a wide variety of applications. In some examples, the deployable rolling joint 100 may be embodied into aerospace applications, minimally invasive medical devices, medical implants, medical insertion or delivery devices, and/or low-cost manufacturing applications such as stowable furniture, etc. The deployable rolling joint 100 may provide a good solution for space-constrained applications, where compact storage is beneficial. For instance, the first deployable joint member 102 and the second deployable joint member 104 may be stored in the compact, undeployed state of FIG. 1B and then deployed into the deployed state. Also, the deployable rolling joint 100 may reduce or eliminate the need for lubrication. In one example, the deployable rolling joint 100 may be used in medical devices where it would be beneficial to have a smaller incision. For example, the incision needed to insert the medical device having the deployable rolling joint 100 may be smaller than the incision needed to insert a joint already in its deployed state. For example, the deployable rolling joint 100 may be positioned in the compact, undeployed state, and then inserted into a body of a patient via an incision. Then, the deployable rolling joint 100 may be moved to the deployed state while inside the body of the patient. The incision used to insert the deployable rolling joint 100 in the compact, undeployed state may be smaller than what would be required if the deployable rolling joint 100 had to be inserted into the body in its deployed state, which has a larger size.

The first deployable joint member 102 may include a first lateral side 103 and a second lateral side 105. The second lateral side 105 may be disposed opposite to the first lateral side 103. In some examples, the first lateral side 103 and/or the second lateral side 105 may be linear or straight. In other examples, the first lateral side 103 and/or the second lateral side 105 may include one or more curved portions or one or more protrusions. The length of the first lateral side 103 may be equal to the length of the second lateral side 105. In other examples, the length of the first lateral side 103 may be different than the length of the second lateral side 105.

The first deployable joint member 102 may include a first end 116 and a second end 117. The second end 117 may be disposed opposite to the first end 116. The first end 116 may include a curved portion. The first end 116 may be a convex curve. The second end 117 may include a curved portion. The second end 117 may be a convex curve. In other examples, the first end 116 and/or the second end 117 is linear. The first end 116 may define a curvature that is the same the curvature of the second end 117. In other examples, the curvature of the first end 116 may be different than the curvature of the second end 117. As shown in FIG. 1A, the length (L) of the first deployable joint member 102 may be defined by the distance between the first lateral side 103 and the second lateral side 105, and the width (W) of the first deployable joint member 102 may be defined by the distance between the first end 116 and the second end 117. As shown in FIG. 1A, because of the curvature of the first and second ends 116, 117, a central portion 119 of the first deployable joint member 102 may have a width that is smaller than widths towards the first lateral side 103 and/or the second lateral side 105.

The first deployable joint member 102 may include a first curved crease 112 forming a first foldable portion 114, and a second curved crease 113 forming a second foldable portion 115. In some examples, one end of the first curved crease 112 may be disposed at the intersection of the first lateral side 103 and the first end 116, and the other end of the first curved crease 112 may be disposed at the intersection of the second lateral side 105 and the first end 116. The first curved crease 112 may define a curvature. In some examples, the curvature of the first curved crease 112 may be larger than the curvature of the first end 116. In some examples, one end of the second curved crease 113 may be disposed at the intersection of the first lateral side 103 and the second end 117, and the other end of the second curved crease 113 may be disposed at the intersection of the second lateral side 105 and the second end 117. The second curved crease 113 may define a curvature. In some examples, the curvature of the second curved crease 113 may be larger than the curvature of the second end 117. The curvature of the second curved crease 113 may be the same as the curvature of the first curved crease 112. In other examples, the curvature of the second curved crease 113 may be different than the curvature of the first curved crease 112.

The first curved crease 112 may have one or more features configured to permit the first foldable portion 114 to bend. The second curved crease 113 may have one or more features configured to permit the second foldable portion 115 to bend. The first foldable portion 114 and the second foldable portion 115 may be configured to bend towards each other, thereby creating a three-dimensional structure having the convex surface portion 108. The first foldable portion 114 may extend between the first curved crease 112 and the first end 116. The second foldable portion 115 may extend between the second curved crease 113 and the second end 117. In some examples, the first curved crease 112 and the second curved crease 113 are valley folds. For instance, when the first foldable portion 114 and the second foldable portion 115 move towards each other, the first deployable joint member 102 is expanded into a three-dimensional structure having the convex surface portion 108 on the bottom of the first deployable joint member 102. For example, referring to FIG. 1A, the surface of the first deployable joint member 102 that extends out of the page forms the concave surface portion 111 of FIG. 1C. The concave surface portion 111 defines a cavity of the first deployable joint member 102. The surface of the first deployable joint member 102 that extends into the page forms the convex surface portion 108. In some examples, portions of the convex surface portion 108 (e.g., the central portion 119 of the convex surface portion 108) may move in an opposite direction to the first and second ends 116, 117 when moving from the flat state to the three-dimensional structure.

The first deployable joint member 102 in the deployed state may have a cylindrical shape with the convex surface portion 108 forming the part of the cylinder in which the convex surface portion 108 of the second deployable joint member 104 rotates. The first foldable portion 114 and the second foldable portion 115 may define the ends of the cylinder. In some examples, the convex surface portion 108 is one half of a cylinder. In some examples, the convex surface portion 108 is a semi-circle. However, the profile of the convex surface portion 108 may have any other type of convex curvature such as an oval or part of a circle instead of a semi-circle. In some examples, the first deployable joint member 102 may be a cam. The convex surface portion 108 may define a first radius (R) of curvature. In the deployed state, the first deployable joint member 102 may define a first height ($H_d$) from the base of the cylinder (e.g. the first end 116) to the convex surface portion 108. The parameters of the first deployable member 102 are further explained with reference to FIGS. 4-5.

The second deployable joint member 104 may be equivalent to the first deployable joint member 102. In some examples, the length (L) and the width (W) of the second deployable joint member 104 may be same as the length (L) and the width (W) of the first deployable joint member 102. In other examples, the length (L) and/or the width (W) of the second deployable joint member 104 may be different from the length (L) and/or the width (W) of the first deployable joint member 102. The second deployable joint member 104 may include a first lateral side 107, a second lateral side 109, a first end 124, a second end 125, a first curved crease 120 forming a first foldable portion 122, and a second curved crease 121 forming a second foldable portion 123, which may include any of the features described above with respect to the first deployable joint member 102. In other examples, the second deployable joint member 104 may be different in one or more dimensions (e.g., width, length, thickness, type of material) from the first deployable joint member 102.

The first foldable portion 122 and the second foldable portion 123 may be configured to rotate towards each other, thereby creating a three-dimensional structure having the convex surface portion 110. In some examples, the first curved crease 120 and the second curved crease 121 are mountain folds. For example, referring to FIG. 1A, the surface of the second deployable joint member 104 that extends out of the page forms the convex surface portion 110 of FIG. 1C. The surface of the second deployable joint member 104 that extends into the page forms a concave surface portion that defines the cavity of the second deployable joint member 104. In some examples, portions of the convex surface portion 110 may move in an opposite direction to the first and second ends 124, 125 when moving from the flat state to the three-dimensional structure. For instance, when the first foldable portion 122 and the second foldable portion 123 move towards each other, the second deployable joint member 104 is transformed into a three-dimensional structure having the convex surface portion 110 on the top of the first deployable joint member 102. The second deployable joint member 104 in the deployed state may have a cylindrical shape with the convex surface portion 110 forming the part of the cylinder in which the convex surface portion 108 of the first deployable joint member 102 may rotate. The first foldable portion 122 and the second foldable portion 123 may define the ends of the cylinder of the second deployable joint member 104.

In the deployed state, the convex surface portion 110 of the second deployable joint member 104 may define a second radius (R) of curvature. In some examples, the first radius (R) of curvature of the convex surface portion 108 may be same as the second radius (R) of curvature of the convex surface portion 110. In other examples, the first radius (R) of curvature may be different than the second radius (R) of curvature. In the deployed state, the second deployable joint member 104 may define a second height ($H_d$) from the base of the cylinder (e.g. the first end 124) to the convex surface portion 110. The second height ($H_d$) of the second deployable joint member 104 may be the same as the first height ($H_d$) of the first deployable joint member 102. In other examples, the second height ($H_d$) of the second deployable joint member 104 may be different than the first height ($H_d$) of the first deployable joint member 102.

The first deployable joint member 102 may be coupled to the second deployable joint member 104 using the plurality of flexures 106. In some examples, the flexures 106 may be flexible bands. In some examples, the flexures 106 are coupled to the first and second deployable joint members 102, 104 such that they do not interfere with one another during the rotating motion in the deployed state. In some examples, the flexures 106 are attached to the first deployable joint member 102 and the second deployable joint member 104 in a manner that all degrees of freedom besides the rolling motion are constrained through contact of the flexures and the first and second deployable joint members 102, 104 or tension in the flexures 106. However, referring to FIG. 1D, the convex surface portions 108, 110 cause an instantaneous axis of rotation path 133 to follow the curvature of the convex surface portions 108, 110. The plurality of flexures 106 may include two or more flexures. In some examples, the plurality of flexures 106 may include a first flexure 106-1, a second flexure 106-2, and a third flexure 106-3, as shown in FIGS. 1A-1C. In other examples, the plurality of flexures 106 may include more than three flexures. In some examples, the flexures 106 may be same with respect to each (e.g., having the same length, width, thickness, size, etc.). In other examples, one or more of the flexures 106 may have at least one different property than another flexure 106. In some examples, as shown in FIG. 1A, the length ($L_{band}$) of each flexure 106 may be the same, but the third flexure 106-3 may have a larger width than the widths of the first flexure 106-1 and the second flexure 106-2.

As shown in FIGS. 1A and 1C, the first flexure 106-1 and the second flexure 106-2 are disposed in parallel and coupled to the second lateral side 105 of the first deployable joint member 102 and the first lateral side 107 of the second deployable joint member 104. The third flexure 106-3 may be coupled to the first lateral side 103 of the first deployable joint member 102 and the second lateral side 109 of the second deployable joint member 104 (although FIG. 1A does not explicitly show the third flexure 106-3 coupled to the second lateral side 109 of the second deployable joint member 104). The first flexure 106-1 and the second flexure 106-2 may be coupled to the first deployable joint member 102 and the second deployable joint member 104 such that they are parallel to each other. Also, the first flexure 106-1 may be sufficiently spaced apart from the second flexure 106-2 such that the third flexure 106-3 can be disposed between the first flexure 106-1 and the second flexure 106-2 in a manner that they do not contact or interfere with each other.

In further detail, the third flexure 106-3 may define a first end portion 130 and a second end portion 132. The first end portion 130 of the third flexure 106-3 may be coupled to the first lateral side 103 of the first deployable joint member 102, and the second end portion 132 may be coupled to the second lateral side 109 of the second deployable joint member 104. The first flexure 106-1 may define a first end portion 138 and a second end portion 140. The first end portion 138 of the first flexure 106-1 may be coupled to the second lateral side 105 of the first deployable joint member 102, and the second end portion 140 of the first flexure 106-1 may be coupled to the first lateral side 107 of the second deployable joint member 104. The second flexure 106-2 may define a first end portion 134 and a second end portion 136. The first end portion 134 of the second flexure 106-2 may be coupled to the second lateral side 105 of the first deployable joint member 102, and the second end portion 136 may be coupled to the first lateral side 107 of the second deployable joint member 104.

The number of attachments on a single joint member may be dependent on the number of flexures 106 used. As shown on FIGS. 1A and 1C, when three flexures 106 are used, there are three attachment points to one joint member. For instance, the first deployable joint member 102 has three attachment points for coupling the flexures 106, e.g., (1) the coupling of the first end portion 130 of the third flexure 106-3 to the first lateral side 103, (2) the coupling of the first end portion 134 of the second flexure 106-2 to the second lateral side 105, and (3) the coupling of the first end portion 138 of the first flexure 106-1 to the second lateral side 105. The second deployable joint member 104 has three attachment points for attaching the flexures 106, e.g., (1) the coupling of the second end portion 132 of the third flexure 106-3 to the second lateral side 109, (2) the coupling of the second end portion 136 of the second flexure 106-2 to the first lateral side 107, and (3) the coupling of the second end portion 140 of the first flexure 106-1 to the first lateral side 107. However, when two flexures are used, there would be two attachment points on each of the first deployable joint member 102 and the second deployable joint member 104. When four flexures are used, there would be four attachment points on each of the first deployable joint member 102 and the second deployable joint member 104.

The actuation of the first deployable joint member 102 from the compact state to the deployed state may be based on a force which pulls the first end 116 and the second end 117 together or through forces which fold the first and second curved creases 112, 113 to the appropriate angles. The actuation of the second deployable joint member 104 may operate in the same manner. In some examples, a mechanical or electro-mechanical actuator may be used to provide the forces to actuate the first deployable joint member 102 and the second deployable joint member 104. In some examples, springs or hand actuation may be used to deploy the deployable rolling joint 100 to the deployed state. In some examples, the first deployable joint member 102 and the second deployable joint member 104 may be self-actuating. For example, the first deployable joint member 102 and the second deployable joint member 104 may include a shape memory material. In some examples, the first deployable joint member 102 and the second deployable joint member 104 may be biased to the deployed state, but held together by a component that can be removed (or moved) when the deployable rolling joint 100 is within a position to be deployed. Then, the component can be removed (or moved) in order to remove the pressure holding the first deployable joint member 102 and the second deployable joint member 104 in the compact state, thereby deploying into the deployed state. In some examples, the shape memory material may include shape memory alloys and/or thermally actuated contractile polymers. In some examples, the first deployable joint member 102 and the second deployable joint member 104 may be moved from the compact state to the deployed state using inflation as an actuator. For instance, the first deployable joint member 102 and the second deployable joint member 104 may include an elastic membrane that is capable of expanding thereby applying a force that actuates the first deployable joint member 102 and the second deployable joint member 104.

FIG. 2A illustrates a deployable rolling joint 200 in a planar state according to another aspect. FIG. 2B illustrates the deployable rolling joint 200 in a compact, undeployed state according to another aspect. FIG. 2C illustrates the deployable rolling joint 200 in a deployed state according to another aspect. The deployable rolling joint 200 may include a first deployable joint member 202, a second deployable joint member 204, and a plurality of flexures 206 coupled to the first deployable joint member 102 and the second deployable joint member 204. In some examples, the first deployable joint member 202, the second deployable joint member 204, and the flexures 206 may include any of the features explained with reference to the first deployable joint member 102, the second deployable joint member 104, and the flexures 106 of FIGS. 1A-1C.

In the planar state of FIG. 2A, the first deployable joint member 202 and the second deployable joint member 204 are relatively flat. The first deployable joint member 202 and the second deployable joint member 204 may include curved creases (e.g., curved creases 212, 213, 220, 221), which allow the first deployable joint member 202 and the second deployable joint member 204 to transition into the deployed state of FIG. 2C. Also, the deployable rolling joint 200 may transition from the planar state of FIG. 2A to the compact, undeployed state of FIG. 2B by folding the first deployable joint member 202 on top of the second deployable joint member 204 (or vice versa) with the flexures 206 disposed between the first deployable joint member 202 and the second deployable joint member 204.

The deployable rolling joint 200 may include stopping members 245 disposed on the second deployable joint member 204. In other examples, the stopping members 245 are disposed on the first deployable joint member 202. In other examples, one or more stopping members 245 are disposed on the first deployable joint member 202, and one or more stopping members 245 are disposed on the second deployable joint member 204. In the compact, undeployed state of FIG. 2B, the stopping members 245 are configured to reduce (or prevent) the first deployable joint member 202 and the second deployable joint member 204 from rotating with respect to each other. For example, the stopping members 245 cause the first and second deployable joint members 202, 204 to interfere with one another when the first deployable joint member 202 or the second deployable joint member 204 tries to rotate in the compact, undeployed state of FIG. 2B.

The first deployable joint member 202 may include a first lateral side 203 and a second lateral side 205. However, unlike the first lateral side 103 of FIGS. 1A-1C, the first lateral side 203 defines a first recessed edge 240, and the second lateral side 205 defines a second recessed edge 241. The length of the first recessed edge 240 may be equal to the length of the second recessed edge 241. In other examples, the length of the first recessed edge 240 may be different than the length of the second recessed edge 241.

The first deployable joint member 202 may include a first end 216 and a second end 217. Each of the first end 216 and the second end 217 may include a convex curve. The first deployable joint member 202 may include a first curved crease 212 forming a first foldable portion 214, and a second curved crease 213 forming a second foldable portion 215. The first foldable portion 214 and the second foldable portion 215 may be configured to bend towards each other, thereby creating a three-dimensional structure having a convex surface portion 208, as shown in FIG. 2C. In some examples, the first curved crease 212 and the second curved crease 213 are valley folds. For instance, when the first foldable portion 214 and the second foldable portion 215 move towards each other, the first deployable joint member 202 is transformed into a three-dimensional structure having the convex surface portion 208 on the bottom of the first deployable joint member 202. The first deployable joint member 202 in the deployed state may have a cylindrical shape with the convex surface portion 208 forming the part of the cylinder in which the convex surface portion 210 of the second deployable joint member 204 rotates. The first foldable portion 214 and the second foldable portion 215 may define the ends of the cylinder.

The second deployable joint member 204 may include the same features as the first deployable joint member 202 with the exception of the stopping members 245 disposed on edge portions of the second deployable joint member 204. The second deployable joint member 104 may include a first lateral side 207 defining a first recessed edge 242, a second lateral side 209 defining a second recessed edge 243, a first curved end 224, a second curved end 225, a first curved crease 220 forming a first foldable portion 222, and a second curved crease 221 forming a second foldable portion 223, which may include any of the features described above with respect to the first deployable joint member 202 or the second deployable joint 104 of FIGS. 1A-1C. In other examples, the second deployable joint member 204 may be different in one or more dimensions (e.g., width, length, thickness, type of material) from the first deployable joint member 202. The first foldable portion 222 and the second foldable portion 223 may be configured to rotate towards each other, thereby creating a three-dimensional structure having the convex surface portion 210. In some examples, the first curved crease 220 and the second curved crease 221 are mountain folds. For instance, when the first foldable portion 222 and the second foldable portion 223 move towards each other, the second deployable joint member 204 is transformed into a three-dimensional structure having the convex surface portion 210 on the top of the second deployable joint member 204.

The first deployable joint member 202 may be coupled to the second deployable joint member 204 using the plurality of flexures 206. The plurality of flexures 206 may include a first flexure 206-1, a second flexure 206-2, and a third flexure 206-3, as shown in FIGS. 2A-2C. The first flexure 206-1 and the second flexure 206-2 are disposed in parallel and coupled to the second recessed edge 241 of the first deployable joint member 202 and the first recessed edge 242 of the second deployable joint member 204. The third flexure 206-3 may be coupled to the first recessed edge 240 of the first deployable joint member 202 and the second recessed edge 243 of the second deployable joint member 204 (although FIG. 2A does not explicitly show the third flexure 206-3 coupled to the second recessed edge 243 of the second deployable joint member 204). The first flexure 206-1 and the second flexure 206-2 may be coupled to the first deployable joint member 202 and the second deployable joint member 204 such that they are parallel to each other. Also, the first flexure 206-1 may be sufficiently spaced apart from the second flexure 206-2 such that the third flexure 206-3 can be disposed between the first flexure 206-1 and the second flexure 206-2 in a manner that they do not contact or interfere with each other.

The stopping members 245 may include a first stopping member 245-1, a second stopping member 245-2, a third stopping member 245-3, and a fourth stopping member 245-4. Referring to FIG. 2A, the first stopping member 245-1 may be coupled to the first lateral side 207 at a first location adjacent to the first recessed edge 242, and the second stopping member 245-2 may be coupled to the first lateral side 207 at a second location adjacent to the first recessed edge 242. Although FIG. 2A depicts the first and second stopping members 245-1, 245-2 extending from the first lateral side 207, the first and second stopping members 245-1, 245-2 are folded back as shown in FIG. 2C. As such, the first and second stopping members 245-1, 245-2 extend from the convex surface portion 210. In some examples, the first and second stopping members 245-1, 245-2 have a thickness that is the same as the thickness of the first and second flexures 206-1, 206-2.

Referring to FIG. 2A, the third stopping member 245-3 may be coupled to the second lateral side 209 at a first location adjacent to the second recessed edge 243, and the fourth stopping member 245-4 may be coupled to the second lateral side 209 at a second location adjacent to the second recessed edge 243. Although FIG. 2A depicts the third and fourth stopping members 245-3, 245-4 extending from the second lateral side 209, the third and fourth stopping members 245-3, 245-4 are folded back in the same manner described above. As such, the third and fourth stopping members 245-3, 245-4 extend from the convex surface portion 210. In some examples, the third and fourth stopping members 245-3, 245-4 have a thickness that is the same as the thickness of the first and second flexures 206-1, 206-2.

Figures 3A, 3B, 3C:
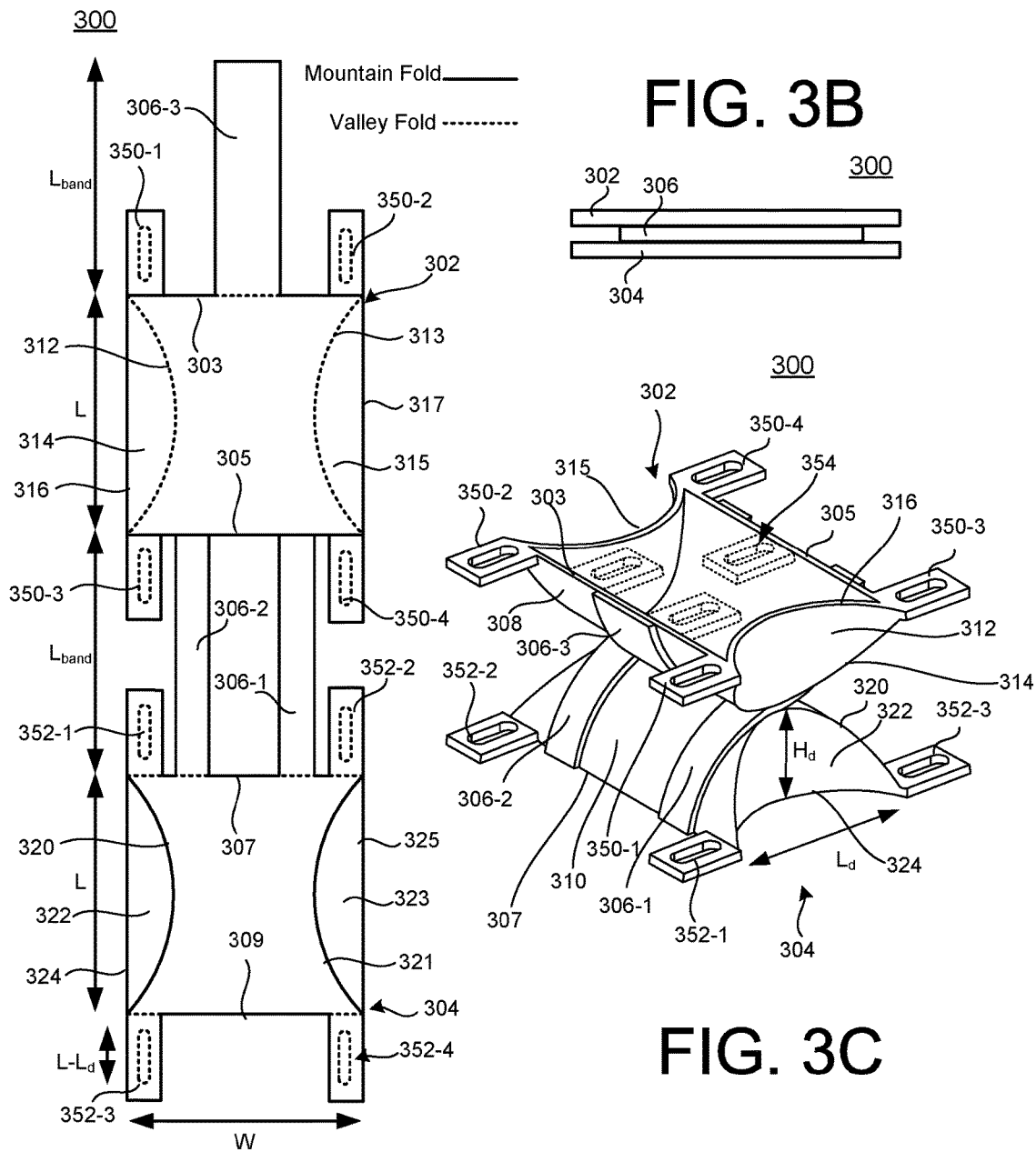
FIG. 3A illustrates the deployable rolling joint in a planar state according to another aspect.
FIG. 3B illustrates the deployable rolling joint in a compact, undeployed state according to another aspect.
FIG. 3C illustrates the deployable rolling joint in a deployed state according to another aspect.

FIGS. 3A-3C illustrates a deployable rolling joint 300 having anchoring members 350, 352 according to an aspect. FIG. 3A illustrates the deployable rolling joint 300 in a planar state according to another aspect. FIG. 3B illustrates the deployable rolling joint 300 in a compact, undeployed state according to another aspect. FIG. 3C illustrates the deployable rolling joint 300 in a deployed state according to another aspect.

The deployable rolling joint 300 may include a first deployable joint member 302, a second deployable joint member 304, and a plurality of flexures 306 coupled to the first deployable joint member 302 and the second deployable joint member 304. In some examples, the first deployable joint member 302, the second deployable joint member 304, and the flexures 306 may include any of the features explained with reference to the first deployable joint member 102, the second deployable joint member 104, and the flexures 106 of FIGS. 1A-1C and/or the first deployable joint member 202, the second deployable joint member 204, and the flexures 206 of FIGS. 2A-2C.

However, in FIGS. 3A-3B, the first deployable joint member 302 may include anchoring members 350, and the second deployable joint member 304 may include anchoring members 352. In examples, anchoring members are disposed on only one of the first deployable joint member 302 and the second deployable joint member 304. In some examples, the anchoring members 350, 352 are disposed on the first deployable joint member 302 and the second deployable joint member 304 in a manner in which the anchoring members 350 do not interfere with the rolling motion in the deployed state. The anchoring members 350, 352 may be any type of component configured to couple the first deployable joint member 302 and the second deployable joint member 304 to device components (e.g., the type and structure of the device components are depend upon the application of the deployable rolling joint 300, which may widely vary). The anchoring members 350 may enable the first deployable joint member 302 to be coupled to a first component (not shown), and the anchoring members 350 may enable the second deployable joint member 304 to be coupled to a second component (not shown), where hinge-type motion is enabled between the first component and the second component when the deployable rolling joint 300 in the deployed state. As shown in FIGS. 3A-3C, the anchoring members 350, 352 may be sliding fits. The sliding fits may be protrusions having through-holes. However, the anchoring members 350, 352 may be any type of structure that is part of an anchoring solution.

The anchoring members 350, 352 may have the same structure with respect to each other, or one or more anchoring members 350, 352 may be different other anchoring members 350, 352. In some examples, the anchoring members 350 are disposed on corner portions of the base of first deployable joint member 302, and the anchoring members 352 are disposed on corner portions of the base of the second deployable joint member 304. In some examples, the anchoring members 350 extend outwardly from the base of the first deployable joint member 302, and the anchoring members 352 extend outwardly from the base of the second deployable joint member 304. In some examples, the first deployable joint member 302 and/or the second deployable joint member 304 include one or more interior anchoring members 354 that extend inwardly from the base of the first deployable joint member 302 and/or the base of the second deployable joint member 304.

The first deployable joint member 302 may include a first lateral side 303 and a second lateral side 305. The first deployable joint member 302 may include a first end 316 and a second end 317. The first deployable joint member 302 may include a first curved crease 312 forming a first foldable portion 314, and a second curved crease 313 forming a second foldable portion 315. The first foldable portion 314 and the second foldable portion 315 may be configured to bend towards each other, thereby creating a three-dimensional structure having a convex surface portion 308, as shown in FIG. 3C.

In some examples, the anchoring members 350 may include a first anchoring member 350-1, a second anchoring member 350-2, a third anchoring member 350-3, and a fourth anchoring member 350-4. However, it is noted that the first deployable joint member 302 may include any number of anchoring members 350 including a single anchoring member 350. In some examples, the first anchoring member 350-1, the second anchoring member 350-2, the third anchoring member 350-3, and the fourth anchoring member 350-4 extend (or are coupled) to different corner portions of the anchoring member 350. In some examples, the anchoring members 350 extend outwardly from the first deployable joint member 302. In some examples, the first anchoring member 350-1 extends from the first lateral side 303 at a first location, and the second anchoring member 350-2 extends from the first lateral side 303 at a second location disposed a distance away from the first location. In some examples, the third anchoring member 350-3 extends from the second lateral side 305 at a first location, and the fourth anchoring member 350-4 extends from the second lateral side 305 at a second location disposed a distance away from the first location.

The second deployable joint member 304 may include the same features as the first deployable joint member 302. In some examples, the second deployable joint member 304 may include one or more different features from the first deployable joint member 302. The second deployable joint member 304 may include a first lateral side 307, a second lateral side 309, a first end 324, a second end 325, a first curved crease 320 forming a first foldable portion 322, and a second curved crease 321 forming a second foldable portion 323, which may include any of the features described above with respect to the first deployable joint member 302. In other examples, the second deployable joint member 304 may be different in one or more dimensions (e.g., width, length, thickness, type of material) from the first deployable joint member 302.

In some examples, the anchoring members 352 may include a first anchoring member 352-1, a second anchoring member 352-2, a third anchoring member 352-3, and a fourth anchoring member 352-4. However, it is noted that the second deployable joint member 304 may include any number of anchoring members 352 including a single anchoring member 352. In some examples, the first anchoring member 352-1, the second anchoring member 352-2, the third anchoring member 352-3, and the fourth anchoring member 352-4 extend (or are coupled) to different corner portions of the second deployable joint member 304. In some examples, the anchoring members 352 extend outwardly from the second deployable joint member 304. In some examples, the first anchoring member 352-1 extends from the first lateral side 307 at a first location, and the second anchoring member 352-2 extends from the first lateral side 307 at a second location disposed a distance away from the first location. In some examples, the third anchoring member 352-3 extends from the second lateral side 309 at a first location, and the fourth anchoring member 352-4 extends from the second lateral side 309 at a second location disposed a distance away from the first location.

Figure 4:
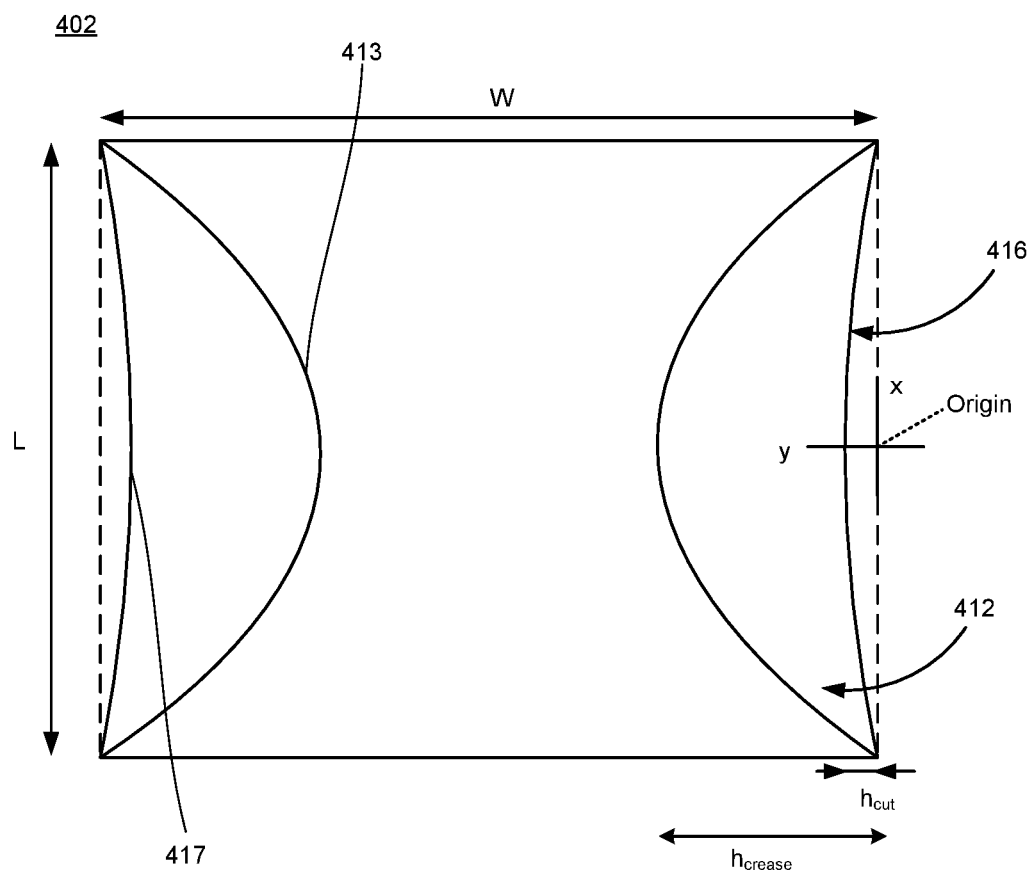
FIG. 4 illustrates a deployable cam in the planar state according to an aspect.
Figures 5A, 5B:
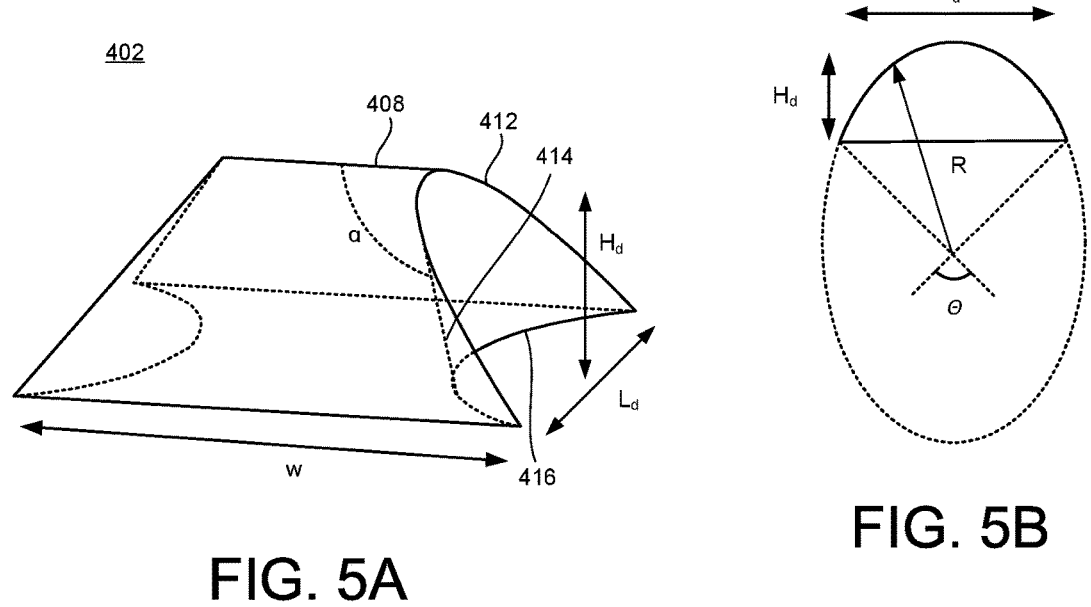
FIG. 5A illustrates a perspective of the deployable cam in the deployed state according to an aspect.
FIG. 5B illustrates a side view of the deployable cam in the deployed state according to an aspect.

FIG. 4 illustrates a deployable cam 402 in the planar state according to an aspect. FIG. 5A illustrates a perspective of the deployable cam 402 in the deployed state. FIG. 5B illustrates a side view of the deployable cam 402 in the deployed state. The deployable cam 402 may the first deployable joint member 102, 202, or 302, and/or the second deployable joint member 104, 204, or 304 as described with respect to the previous figures. The geometry of curved creases 412, 413 used to form the deployable cam 402 as well as the length of the flexures (e.g., flexures 106, 206, or 306) may determine the range of motion for the angular deflection of the deployable rolling joint and the radius R of the deployable cam 402 in the deployed state.

The following relationships were developed for the deployable rolling joint such that the radius of the deployable cam 402, R, the deflection of the joint, Θ, the angle between cam side 414 (e.g., foldable portion 114, 214, or 314) and face 408 (e.g., convex surface portion 108, 208, or 308), α, and the width of the deployable cam 400, W, are selected all other parameters of the deployable rolling joint are computed. After selecting the radius of the deployable cam, R, and the desired angular deflection of the joint, Θ, which can range from 0 to 180 degrees, the required panel length, L, can be calculated by $$L = R\Theta\left(\frac{\pi}{180}\right) \qquad \text{Eq. (1)}$$

It is noted that the addition of the stopping members 245 of FIGS. 2A-2C may cause the effective angular defection of the joint to be decreased to:

$$\Theta_{config2} = \frac{L_{band}}{R}\left(\frac{180}{\pi}\right) \qquad \text{Eq. (2)}$$

Using the selected angle in degrees between the cam face 408 and cam side 414 in the deployed state, α, the height of the crease, $h_{crease}$, is computed as follows:

$$h_{crease} = R\left(\tan\left(\frac{\alpha}{2}\right)\right) \qquad \text{Eq. (3)}$$

The height of the curved cut edge of the panel, $h_{cut}$, when α is in degrees is decreased as:

$$h_{cut} = R(\tan(\alpha - 90)) \qquad \text{Eq. (4):}$$

The crease geometry, which corresponds to the unwrapped curve of a cylinder cut by a plane, can be expressed by the following:

$$y_{crease} = h_{crease}\left(\cos\left(\frac{x}{R}\right) - \cos\left(\frac{L}{2R}\right)\right) \quad \text{Eq. (5)}$$

The domain for X is from −(L/2) to (L/2). Similarly, the curved cut edge geometry, can be expressed by the following equation:

$$y_{cut} = h_{cut}\left(\cos\left(\frac{x}{R}\right) - \cos\left(\frac{L}{2R}\right)\right) \quad \text{Eq. (6)}$$

The length, $L_d$, of the deployable cam 402 in the deployed state is expressed as:

$$L_d = 2R\left(\sin\left(\frac{\Theta}{2}\right)\right) \quad \text{Eq. (7)}$$

The height, $H_d$, of the deployable joint member 402 in the deployed state is computed from:

$$H_d = R - R\left(\cos\left(\frac{\Theta}{2}\right)\right) \quad \text{Eq. (8)}$$

Figure 6A:
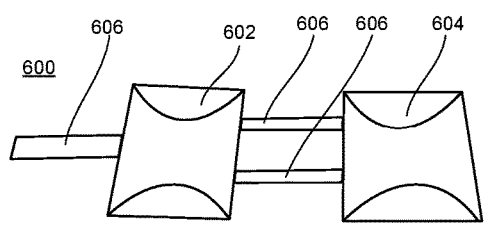
FIG. 6A illustrates an example of a deployable rolling joint in the planar state according to an aspect.
Figure 6B:
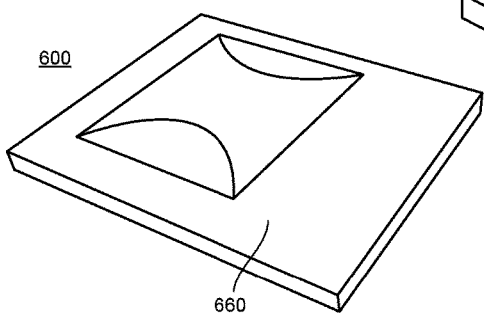
FIG. 6B illustrates an example of the deployable rolling joint in the compact state according to an aspect.
Figure 6C:
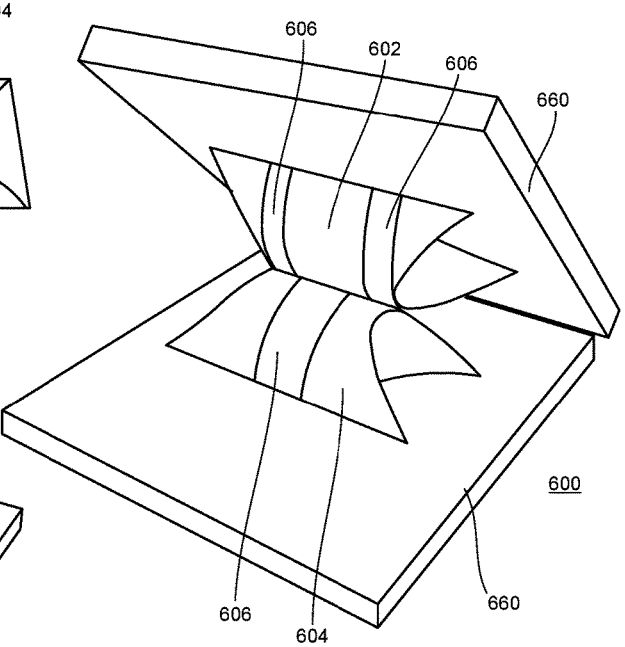
FIG. 6C illustrates an example of the deployable rolling joint in the deployed state according to an aspect.

FIG. 6A illustrates an example of a deployable rolling joint 600 in the planar state according to an aspect. FIG. 6B illustrates an example of the deployable rolling joint 600 in the compact state according to an aspect. FIG. 6C illustrates an example of the deployable rolling joint 600 in the deployed state according to an aspect. In some examples, the deployable rolling joint 600 may be the deployable rolling joint 100 of FIGS. 1A-1C. The deployable rolling joint 600 may be constructed with 0.38 mm (0.015 in) thick polycarbonate panels 602, 604 with 0.023 mm (9 mils) thick metallic glass hinges 606. Bulk metallic glasses are metallic alloys which fail to crystallize during solidification. This gives them a unique combination of properties including high elastic strain and strength, making them a good candidate for complaint applications. The metallic glass was secured with adhesive transfer tape between two layers of polycarbonate panels from which material in the curved crease regions had been removed. The joint was anchored to foamboard panels 660 by polycarbonate tabs that where inserted into slits in the foamboard.

Figure 7A:
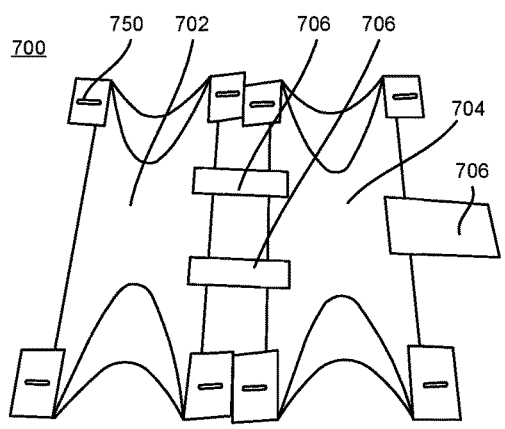
FIG. 7A illustrates a deployable rolling joint according to another aspect.
Figure 7B:
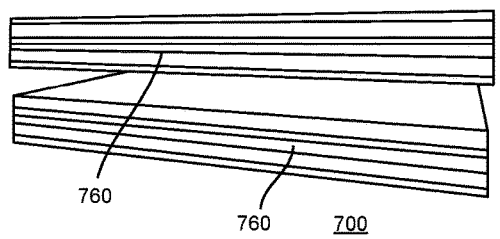
FIG. 7B illustrates an example of the deployable rolling joint in the compact state according to another aspect.
Figure 7C:
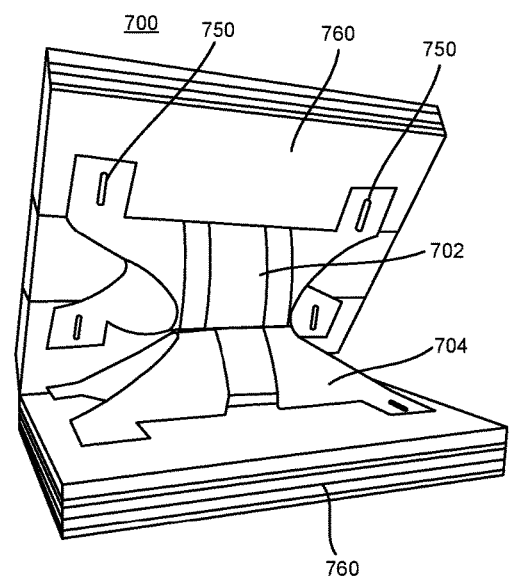
FIG. 7C illustrates an example of the deployable rolling joint in the deployed state according to another aspect.

FIG. 7A illustrates an example of a deployable rolling joint 700 according to another aspect. FIG. 7B illustrates an example of the deployable rolling joint 700 in the compact state according to another aspect. FIG. 7C illustrates an example of the deployable rolling joint 700 in the deployed state according to another aspect. In some examples, the deployable rolling joint 700 may be the deployable rolling joint 200 of FIGS. 2A-2C. The deployable rolling joint 700 having a first joint member 702, a second joint member 704, and flexures 706 may be constructed from a 0.81 mm (0.032 in) polypropylene sheet. The curved creases and creases where the flexures 706 and sliding fits 750 connect to the first and second joint members 702, 704 were created by using an embossing tool to remove material to form living hinges in the polypropylene. The polypropylene was folded and secured to wooden panels 760 with nails to compete the sliding fits 750. Polypropylene tabs on the base of the first and second joint members 702, 704 were inserted into grooves in the wood panels to lock the joint into the deployed state. The deployed joint functioned under a 100 N (22.5 lb) compressive load before visually detectable deformation of the cams occurred.

FIGS. 8A-8C illustrate a deployable translating platform assembly 800 according to an aspect. FIG. 8A illustrates a first deployable joint member 802 in a planar state that is used in the deployable translating platform assembly 800 according to an aspect. FIG. 8B illustrates a deployable translating platform assembly 800 in an assembled, but undeployed state according to an aspect. FIG. 8C illustrates the deployable translating platform assembly 800 in a deployed state according to an aspect.

The deployable translating platform assembly 800 may include first and second deployable joint units 875-1, 875-2 coupled to and disposed between a first platform 860-1 and a second platform 860-2. The first platform 860-1 and the second platform 860-2 may be rectangular panels. However, the first platform 860-1 and the second platform 860-2 may have any type of shape.

In other examples, the deployable translating platform assembly 800 may include only one deployable joint unit (e.g., either the first deployable joint unit 875-1 or the second deployable joint unit 875-2). The first and second deployable joint units 875-1, 875-2 are configured to expand and contract such that the first platform 860-1 moves away from the second platform 860-2 (or vice versa). In some examples, the first platform 860-1 moves linearly away from the second platform 860-2 (or vice versa). In other examples, the first platform 860-1 and the second platform 860-2 do not linearly move away from each other, but move at an angle with respect to each other. In some examples, the first deployable joint unit 875-1 is configured to move from the compact state of FIG. 8B to the deployed state of FIG. 8C by expanding by a first distance. In some examples, the second deployable joint unit 875-2 is configured to move from the compact state of FIG. 8B to the deployed state of FIG. 8C by expanding by a second distance. In some examples, the second distance is equal to the first distance. In other examples, the second distance is different than the first distance such that one portion of the first platform 860-1 moves a greater or less distance than another portion of the first platform 860-1. In some examples, the first deployable joint unit 875-1 and the second deployable joint unit 875-2 are configured to expand at the same time when moving to the deployed state. In other examples, the first deployable joint unit 875-1 and the second deployable joint unit 875-2 are configured to expand at different times.

In some examples, the first and second deployable joint units 875-1, 875-2 may include an inverted arrangement of the first deployable joint member 102, 202, or 302, and the second deployable joint member 104, 204, or 304 such that the first platform 860-1 can translate away from the second platform 860-2. In some examples, the deployable translating platform assembly 800 may have the ability to be stored flat with effectively no degrees of freedom and to deploy to a state where linear translation is facilitated. For example, in the deployed state, the first and second deployable joint units 875-1, 875-2 may operate as rollers such that the first platform 860-1 and the second platform 860-2 can independently translate in a first direction $D_1$ and a second direction $D_2$. In some examples, the first direction $D_1$ and the second direction $D_2$ are opposite to each other.

Each of the first deployable joint unit 875-1 and the second deployable joint unit 875-2 may include a first deployable joint member 802 having flexures 806 coupled to the first platform 860-1, and a second deployable joint member 804 having flexures 806 coupled to the second platform 860-2. For instance, each of the first deployable joint unit 875-1 and the second deployable joint unit 875-2 may include a pair of joint members, where the pair includes the first deployable joint member 802 and the second deployable joint member 804. The flexures 806 of the first deployable joint member 802 are coupled to the first platform 860-1, and the flexures 806 of the second deployable joint member 804 are coupled to the second platform 860-2. In some examples, the components of the second deployable joint unit 875-2 are identical to the components of the first deployable joint unit 875-1. In other examples, one or more of the components of the second deployable joint unit 875-2 are different from the components of the first deployable joint unit 875-1.

In the compact state of FIG. 8B, each pair of the first deployable joint 802 and the second deployable joint member 804 are in a flat, linear configuration. In some examples, in the compact state of FIG. 8B, each of the first deployable joint unit 875-1 and the second deployable joint unit 875-2 may have four layers between the first platform 860-1 and the second platform 860-2. For example, with respect to the first deployable joint unit 875-1, the four layers (starting from the bottom) may include the first deployable joint member's flexures 806, the first deployable joint member 802 in the flat, linear configuration, the second deployable joint member 804 in the flat, linear configuration, and the second deployable joint member's flexures 806.

FIG. 8A illustrates the first deployable joint member 802 coupled to the flexures 806 in the planar state. The first deployable joint member 802 may be similar to any of the deployable joint members explained with reference to the previous figures. However, attachment portions 870 may extend from end portions of the flexures 806, and the attachment portions 870 are coupled to a surface of the first platform 860-1. Also, in some examples, the cylinder profile (e.g. the profile of a convex surface portion 808) of the first deployable joint member 802 is a half circle to enable 180 degrees of angular rotation.

The first deployable joint member 802 may include a first lateral side 803 and a second lateral side 805. The second lateral side 805 may be disposed opposite to the first lateral side 803. In some examples, the first lateral side 803 and/or the second lateral side 805 may be linear or straight. In other examples, the first lateral side 803 and/or the second lateral side 805 may include curved portion(s) or protrusion(s). The length of the first lateral side 803 may be equal to the length of the second lateral side 805. In other examples, the length of the first lateral side 803 may be different than the length of the second lateral side 805.

The first deployable joint member 802 may include a first end 816 and a second end 817. The second end 817 may be disposed opposite to the first end 816. In some examples, the first end 816 and/or the second end 817 are curved. In other examples, the first end 816 and/or the second end 817 are linear or straight. As shown in FIG. 8A, the length (L) of the first deployable joint member 802 may be defined by the distance between the first lateral side 803 and the second lateral side 805, and the width (W) of the first deployable joint member 802 may be defined by the distance between the first end 816 and the second end 817.

The first deployable joint member 802 may include a first curved crease 812 forming a first foldable portion 814, and a second curved crease 813 forming a second foldable portion 815. In some examples, one end of the first curved crease 812 may be disposed at the intersection of the first lateral side 803 and the first end 816, and the other end of the first curved crease 812 may be disposed at the intersection of the second lateral side 805 and the first end 816. The first curved crease 812 may define a curvature. In some examples, one end of the second curved crease 813 may be disposed at the intersection of the first lateral side 803 and the second end 817, and the other end of the second curved crease 813 may be disposed at the intersection of the second lateral side 805 and the second end 817. The second curved crease 813 may define a curvature. In some examples, the curvature of the second curved crease 813 may be larger than the curvature of the second end 817. The curvature of the second curved crease 813 may be the same as the radius of curvature of the first curved crease 812. In other examples, the radius of curvature of the second curved crease 813 may be different than the radius of curvature of the first curved crease 812.

The first curved crease 812 may have one or more features configured to permit the first foldable portion 814 to bend. The second curved crease 813 may have one or more features configured to permit the second foldable portion 815 to bend. In some examples, the first curved crease 812 and the second curved crease 813 are mountain folds as shown on FIG. 8A. The first foldable portion 814 and the second foldable portion 815 may be configured to move towards each other (via their respective creases), thereby creating a three-dimensional structure having the convex surface portion 808. The first deployable joint member 802 in the deployed state may have a cylindrical shape with the convex surface portion 808 forming the part of the cylinder in which the convex surface portion 110 of the second deployable joint member 104 rotates. The first foldable portion 114 and the second foldable portion 115 may define the ends of the cylinder.

The first deployable joint member 802 may be coupled to the second deployable joint member 804. The second deployable joint member 804 may include the same features previously explained with reference to the first deployable joint member 802. In some examples, the first and second lateral sides 803, 805 of the first deployable joint member 802 and the second deployable joint member 804 are coupled together (e.g., only two of the four sides are coupled together). For example, the first lateral side 803 of the first deployable joint member 802 may be coupled to the first lateral side 803 of the second deployable joint member 804, and the second lateral side 805 of the first deployable joint member 802 may be coupled to the second lateral side 805 of the second deployable joint member 804. In other examples, four edges of one joint member are coupled to four edges of another joint member. For example, in addition to the lateral sides, the first end 816 of the first deployable joint member 802 may be coupled to the first end 816 of the second deployable joint member 804, and the second end 817 of the first deployable joint member 802 may be coupled to the second end 817 of the second deployable joint member 804.

The first deployable joint member 802 may be coupled to the first platform 860-1 using the flexures 806. In some examples, the flexures 806 may be flexible bands. In some examples, the first deployable joint member 802 may be coupled to the first platform 860-1 using a first flexure 806-1, a second flexure 806-2, and a third flexure 806-3. In other examples, the first deployable joint member 802 is coupled to the first platform 860-1 using less than three flexures 806. In other examples, the first deployable joint member 802 is coupled to the first platform 860-1 using more than four flexures 806. In some examples, the flexures 806 used to couple the first deployable joint member 802 to the first platform 860-1 may be same with respect to each other (e.g., having the same length, width, thickness, size, etc.). In other examples, one or more of the flexures 806 may have at least one different property than another flexure 806. As shown in FIG. 8C, the second deployable joint member 804 may be coupled to the second platform 860-2 using three flexures 806 (e.g., the first flexure 806-1, the second flexure 806-2, and the third flexure 806-3). In some examples, the second deployable joint member 804 is coupled to the second platform 860-2 in the same manner described with reference to the first deployable joint member 802.

The first flexure 806-1 and the second flexure 806-2 are disposed in parallel and coupled to the second lateral side 805 of the first deployable joint member 802. The third flexure 806-3 may be coupled to the first lateral side 803 of the first deployable joint member 802. In further detail, the third flexure 106-3 may define a first end portion 830 and a second end portion 832. The first end portion 830 of the third flexure 806-3 may be coupled to the first lateral side 803 of the first deployable joint member 802. The attachment portion 870 may extend from the second end portion 832 of the third flexure 806-3. In some examples, the attachment portion 870 may be a portion of the third flexure 806-3 that is used to attach to the first platform 860-1. In other examples, the attachment portion 870 may be a separate component that is coupled to the second end portion 832 of the third flexure 806-3. The first flexure 806-1 may define a first end portion 838 and a second end portion 840. The first end portion 838 of the first flexure 806-1 may be coupled to the second lateral side 805 of the first deployable joint member 802. The attachment portion 870 may extend from the second end portion 840 of the first flexure 806-1. In some examples, the attachment portion 870 may be a portion of the first flexure 806-1 that is used to attach to the first platform 860-1. In other examples, the attachment portion 870 may be a separate component that is coupled to the second end portion 840 of the first flexure 806-1. The second flexure 806-2 may define a first end portion 834 and a second end portion 836. The first end portion 834 of the second flexure 806-2 may be coupled to the second lateral side 805 of the first deployable joint member 802. The attachment portion 870 may extend from the second end portion 836 of the second flexure 806-2. In some examples, the attachment portion 870 may be a portion of the second flexure 806-2 that is used to attach to the first platform 860-1. In other examples, the attachment portion 870 may be a separate component that is coupled to the second end portion 836 of the second flexure 806-2.

The range of linear translation, δ, may be expressed in terms of the radius, R, of the first deployable joint member 102 (e.g., the radius of curvature of the convex surface portion 808), as follows:

$$\delta = \pi R \quad \text{Eq. (9):}$$

This range may be adjusted to a shorter length by shortening the length ($L_{band}$) of the flexures 806. The cam geometry and curved crease geometry may be described with reference to Eqs. (1), (3), (5), (7), and (8), where $\Theta = 180$ degrees. Referring to FIGS. 4 and 8C, if α<135 degrees, the joined deployable joint members 802, 804 may need to be actuated at separate times to avoid interface of the side panels (e.g., the foldable portions 814, 815). If α>135 degrees, the joined deployable joint members 802, 804 may be actuated simultaneously and all edges of the first and second deployable joint members 802, 804 can be joined together instead of only the opposite edges. Also, it is noted that that the motion that occurs during deployment of the deployable translating platform assembly 800 may not require sliding fits to anchor the first and second deployable joint members 802, 804 because the first and second deployable joint members 802, 804 can be anchored to the first and second platforms 860-1, 860-2 by the flexures 806.

Figure 9:
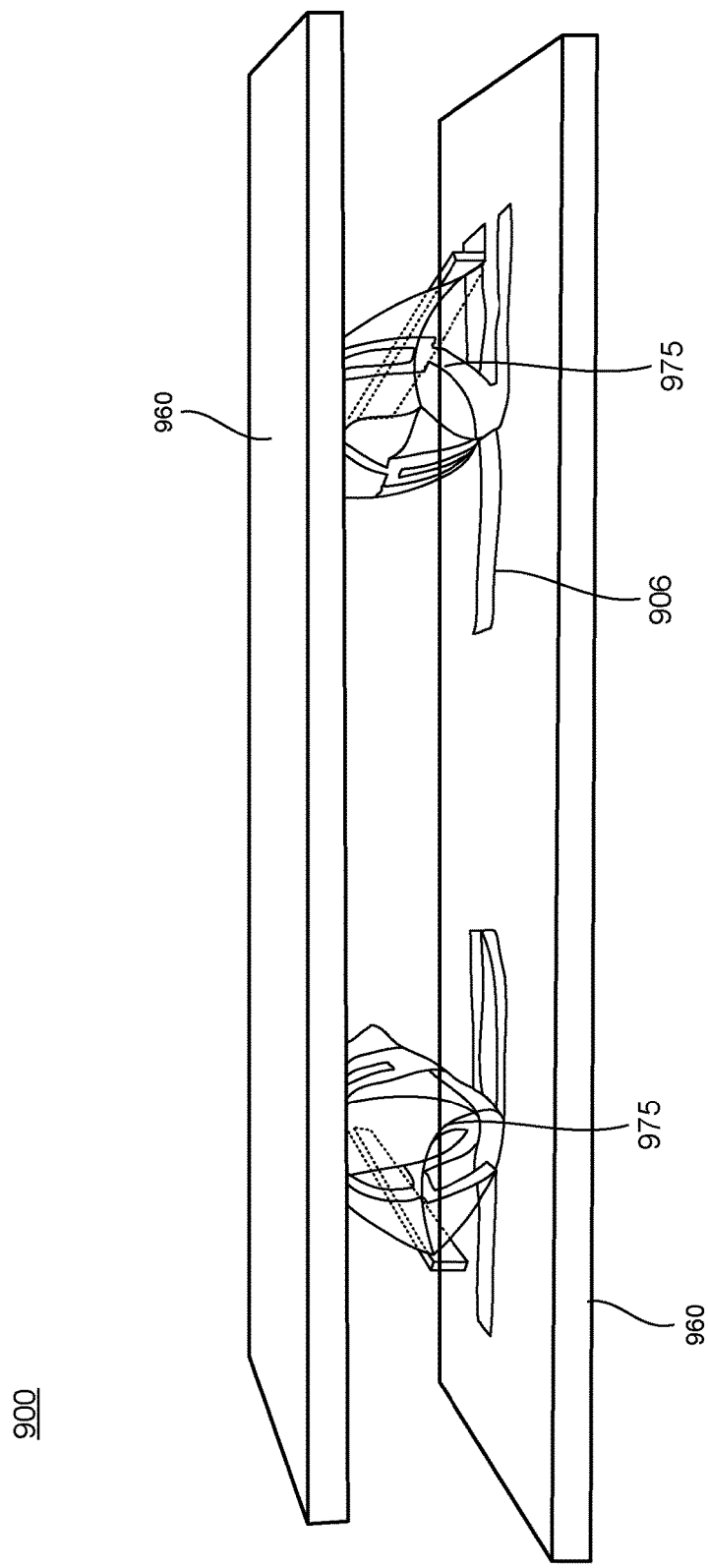
FIG. 9 illustrates an example of a deployable translating platform assembly according to an aspect.

FIG. 9 illustrates an example of a deployable translating platform assembly 900 according to an aspect. The deployable translating platform assembly 900 may be the deployable translating platform assembly 800 of FIGS. 8A-8C. The deployable translating platform assembly 900 may be constructed from deployable cams 975 made of 0.38 mm (0.015 in) polycarbonate sheets and connected to foamboard translating panels 960 via flexible bands 906. A small piece of wood and mono-filaments may be used to lock the mechanism into the deployed state.

Figure 10:
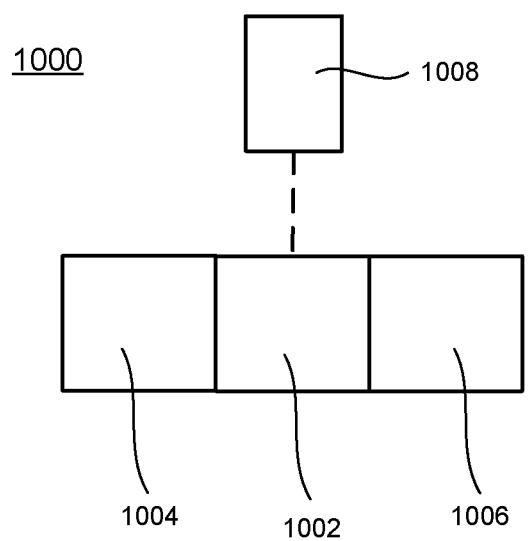
FIG. 10 illustrates a device having a deployable joint according to an aspect.

FIG. 10 illustrates a device 1000 having a deployable joint 1002 according to an aspect. The device 1000 may be used in a wide variety of applications. In some examples, the device 1000 may be used in aerospace applications, and/or low-cost manufacturing applications such as stowable furniture, etc. In some examples, the device 1000 is a medical device. For example, the device 1000 configured as the medical device may be an insertion device for minimally invasive surgery and/or a medical implant such as a spinal implant. The deployable joint 1002 may be the deployable rolling joint 100, 200, or 300, or the deployable translating platform assembly 800. The device 1000 may include a first portion 1004 and a second portion 1006. The deployable joint 1002 may be disposed between and coupled to the first portion 1004 and the second portion 1006 such that the first portion 1004 may rotate or translate with respect to the second portion 1006. In some examples, the anchoring members 350 of FIG. 3C may be coupled to the first portion 1004, and the anchoring members 352 may be coupled to the second portion 1006. In some examples, referring to FIGS. 8B and 8C, the first platform 860-1 may be coupled to the first portion 1004, and the second platform 860-2 may be coupled to the second portion 1006. In other examples, the first platform 860-1 and the second platform 860-2 form portions of the device 1000 itself in which the first platform 860-1 and the second platform 860-2 may be the first portion 1004 and the second portion 1006, respectively.

The deployable joint 1002 may move from a compact, undeployed state to a deployed state in the manner as described with reference to the previous figures. In some examples, the device 1000 may have an actuator 1008 configured to move the deployable joint 1002 from the compact, undeployed state to the deployed state. For example, the actuator 1008 may be configured to apply one or more forces on the deployable joint 1002 to move from the compact, undeployed state to the deployed state. Referring to FIGS. 1B-1C and 10, the actuator 1008 may apply a force which pulls the first end 116 and the second end 117 together and/or apply forces which fold the first and second curved creases 112, 113 to the appropriate angles. In some examples, the actuator 1008 may include one or more cable members configured to apply the forces on the deployable joint 1002. In some examples, the actuator 1008 may include an inflation mechanism configured to inflate the deployable joint 1002 to the deployed state. In other examples, the deployable joint 1002 may be self-actuating. For example, the deployable joint 1002 may include a shape memory material capable of self-actuating to the deployed state. In some examples, the shape memory material may include shape memory alloys and/or thermally actuated contractile polymers. The actuator 1008 and/or self-deploying joint may be beneficial from some medical devices such as a medical insertion device, medical delivery device, or medical implants. For example, the device 1000 may be inserted into the body via an incision with the deployable joint 1002 in the compact, undeployed state, and then the deployable joint 1002 may be actuated to the deployed state while inside the body using the actuator 1108 (or the deployable joint 1002 self-actuates).

Figure 11:
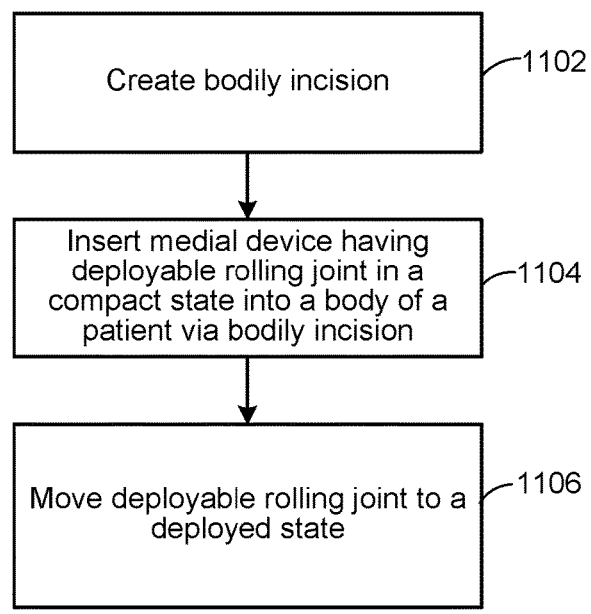
FIG. 11 is a flowchart illustrating operations for inserting a medical device having a deployable rolling joint into a body of a patient according to an aspect.

FIG. 11 is a flowchart 1100 illustrating operations for inserting a medical device having a deployable rolling joint into a body of a patient according to an aspect. Although the flowchart 1100 illustrates the operations in sequential order, it will be appreciated that this is merely an example, and that additional or alternative operations may be included. Further, operations of FIG. 11 and related operations may be executed in a different order than that shown, or in a parallel or overlapping fashion.

A bodily incision may be created (1102), and a medical device having the deployable rolling joint in the compact state may be inserted into a body of a patient via the bodily incision. The medical device may be any type of medical device capable of being inserted into a body. In some examples, the medical device is a medical delivery device, an insertion device, or a medical implant. In some examples, the medical device may be the device 1000 having the deployable rolling joint 100, 200, or 300. In the compact state and using the deployable rolling joint 100 as an example, the first deployable joint member 102 and the second deployable joint member 104 are relatively flat or in a linear configuration, which causes the medical device to have a size smaller. Then, the deployable rolling joint 100 may be moved to the deployed state while the medical device is disposed within the body of the patient (1106). For example, referring to FIG. 10, the actuator 1008 may be actuated to apply one or more forces on the deployable rolling joint 100 to move from the compact, undeployed state to the deployed state. In other examples, the deployable rolling joint 100 is configured to self-actuate to the deployed state. Then, the medical device may operate according to its intended purpose while in the deployed state. In some examples, the deployable rolling joint 100 may be moved from the deployed to the compact, undeployed state. For example, referring to FIG. 10, the actuator 1008 may be actuated to apply one or more forces on the deployable rolling joint 100 to move from the deployed state to the compact, undeployed state. In other examples, the deployable rolling joint 100 is configured to self-deactivate from the deployed state to the compact, undeployed state. Then, the medical device having the deployable rolling joint 100 in the compact, undeployed state may be removed from the body of the patient via the same incision used to insert the medical device or a separate exit incision.

Figure 12:
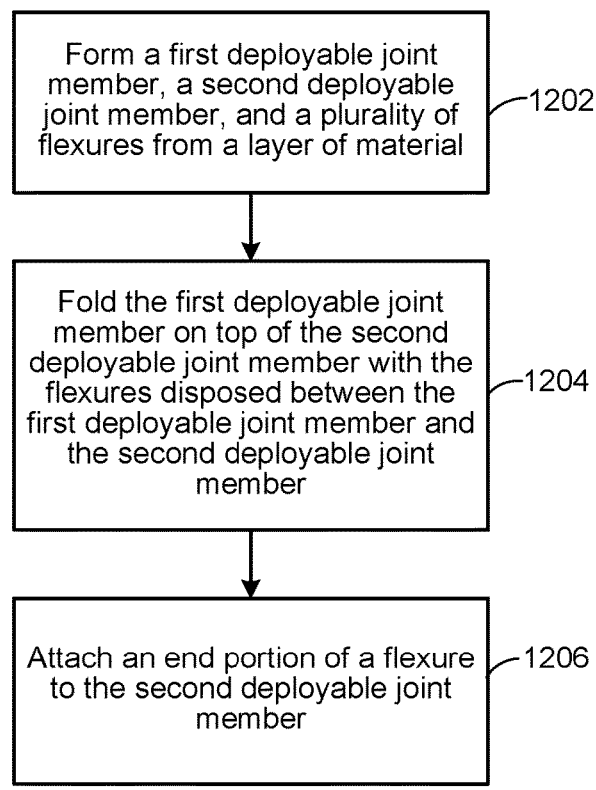
FIG. 12 is a flowchart illustrating operations for manufacturing and assembling a deployable rolling joint according to an aspect.

FIG. 12 is a flowchart 1200 illustrating operations for manufacturing and assembling a deployable rolling joint according to an aspect. Although the flowchart 1200 illustrates the operations in sequential order, it will be appreciated that this is merely an example, and that additional or alternative operations may be included. Further, operations of FIG. 12 and related operations may be executed in a different order than that shown, or in a parallel or overlapping fashion. The deployable rolling joint may be the deployable rolling joint 100, 200, or 300. Although the flowchart 1200 is explained with reference to the deployable rolling joint 100, it is noted that the deployable rolling joint may be the deployable rolling joint 200 or 300.

A first deployable joint member, a second deployable joint member, and a plurality of flexures may be formed from a layer of material (1202). For example, a single, continuous layer of material in the planar state may be machine processed to form the first deployable joint member 102, the second deployable joint member 104, and the plurality of flexures 106. As such, the first deployable joint member 102, the second deployable joint member 104, and the plurality of flexures 106 may be integrally formed. Also, the machine processing may create the curved creases (112, 113, 120, 121). The first deployable joint member 102 may be folded on top of the second deployable joint member 104 with the flexures 106 disposed between the first deployable joint member 102 and the second deployable joint member 104 in a manner as shown in FIG. 1B (1204). Then, in order to complete the assembly, an end portion of a flexure extending from the first deployable joint member 102 may be attached to the second deployable joint member 104 (1206). For instance, the second end portion 132 of the third flexure 106-3 may be coupled to the second lateral side 109 of the second deployable joint member 104.

Figure 13:
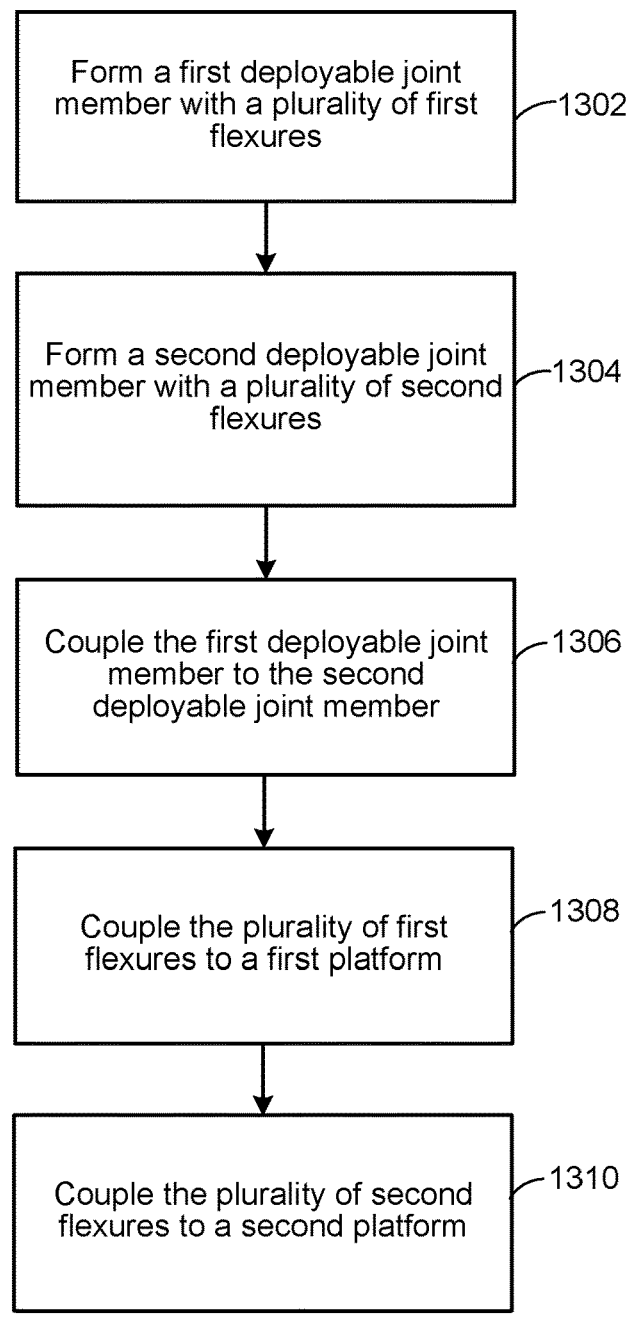
FIG. 13 is a flowchart illustrating operations for manufacturing and assembling a deployable translating platform assembly according to an aspect.

FIG. 13 is a flowchart 1300 illustrating operations for manufacturing and assembling a deployable translating platform assembly according to an aspect. Although the flowchart 1300 illustrates the operations in sequential order, it will be appreciated that this is merely an example, and that additional or alternative operations may be included. Further, operations of FIG. 13 and related operations may be executed in a different order than that shown, or in a parallel or overlapping fashion. The deployable translating platform assembly may be the deployable translating platform assembly 800.

A first deployable joint member with a plurality of first flexures may be formed (1302), and a second deployable joint member with a plurality of second flexures may be formed (1304). For example, the first deployable joint member 802 with the plurality of flexures 806 may be formed from a layer of material. For example, a single, continuous layer of material in the planar state may be machine processed to form the first deployable joint member 802 with the plurality of flexures 806. Also, the second deployable joint member 804 with the plurality of flexures 806 may be formed from a layer of material. For example, a single, continuous layer of material in the planar state may be machine processed to form the second deployable joint member 804 with the plurality of flexures 806. In some examples, the first deployable joint member 802 with the plurality of flexures 806 may be formed from a separate layer of material from the second deployable joint member 804 with the plurality of flexures 806. In other examples, the first deployable joint member 802, the second deployable joint member 804, and the flexures 806 may be formed from a single, continuous sheet of material in the planar state.

The first deployable joint member may be coupled to the second deployable joint member (1306). For example, the first deployable joint member 802 may be coupled to the second deployable joint member 804. In particular, the first and second lateral sides 803, 805 of the first deployable joint member 802 and the second deployable joint member 804 may be coupled together (e.g., only two of the four sides are coupled together). In other examples, four edges of one joint member may be coupled to four edges of another joint member. For example, in addition to the lateral sides, the first end 816 of the first deployable joint member 802 may be coupled to the first end 816 of the second deployable joint member 804, and the second end 817 of the first deployable joint member 802 may be coupled to the second end 817 of the second deployable joint member 804.

The plurality of first flexures may be coupled to the first platform (1308). For example, the first deployable joint member 802 may be coupled to the first platform 860-1 using the flexures 806 of the first deployable joint member 802. The plurality of second flexures may be coupled to the second platform (1310). For example, the second deployable joint member 804 may be coupled to the second platform 860-2 using the flexures 806 of the second deployable joint member 804.

It is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the embodiments.

It will also be understood that when an element, such as a layer, a region, or a substrate, is referred to as being on, connected to, electrically connected to, coupled to, or electrically coupled to another element, it may be directly on, connected or coupled to the other element, or one or more intervening elements may be present. In contrast, when an element is referred to as being directly on, directly connected to or directly coupled to another element or layer, there are no intervening elements or layers present. Although the terms directly on, directly connected to, or directly coupled to may not be used throughout the detailed description, elements that are shown as being directly on, directly connected or directly coupled can be referred to as such. The claims of the application may be amended to recite exemplary relationships described in the specification or shown in the figures.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically. Accordingly, a singular form may, unless definitely indicating a particular case in terms of the context, include a plural form. Spatially relative terms (e.g., over, above, upper, under, beneath, below, lower, and so forth) are intended to encompass different orientations of the device in use or operation in addition to the orientation depicted in the figures. In some implementations, the relative terms above and below can, respectively, include vertically above and vertically below. In some implementations, the term adjacent can include laterally adjacent to or horizontally adjacent to.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the implementations. It should be understood that they have been presented by way of example only, not limitation, and various changes in form and details may be made. Any portion of the apparatus and/or methods described herein may be combined in any combination, except mutually exclusive combinations. The implementations described herein can include various combinations and/or sub-combinations of the functions, components and/or features of the different implementations described.

What is claimed is:

1. A device comprising:
  a deployable rolling joint including:
    a first deployable joint member;
    a second deployable joint member; and
    a plurality of flexures coupled to the first deployable joint member and the second deployable joint member,
  the deployable rolling joint configured to move from a compact state to a deployed state, the compact state being state in which the first deployable joint member is substantially flat, the second deployable joint member is substantially flat, and the first deployable joint member, the second deployable joint member, and the plurality of flexures are stacked on top of each other, the deployed state being a state in which the first deployable joint member forms a convex surface portion and the second deployable joint member forms a convex surface portion,
  in response to the deployable rolling joint being in the deployed state, the convex surface portion of the first deployable joint member configured to roll with respect the convex surface portion of the second deployable joint member, the plurality of flexures being configured to hold the first deployable joint member and the second deployable joint member together as the first deployable joint member and the second deployable joint member roll across each other.

2. The device of claim 1, wherein, in response to the deployable rolling joint being in the compact state, the plurality of flexures are disposed between the first deployable joint member and the second deployable joint member.

3. The device of claim 1, wherein the first deployable joint member, the second deployable joint member, and the plurality of flexures are integrally formed from a single, continuous sheet of material.

4. The device of claim 1, wherein each of the first deployable joint member and the second deployable joint member includes a first curved crease firming a first foldable portion, and a second curved crease forming a second foldable portion, the first foldable portion and the second foldable portion configured to bend toward each other via the first curved crease and the second curved crease to move from the compact state to the deployed state.

5. The device of claim 1, wherein the first deployable joint member includes a memory shape material, the memory shape material biasing the first deployable joint member to the deployed state.

6. The device of claim 1, wherein the device is a medical device having a first portion and a second portion, the first deployable joint member being coupled to the first portion of the medical device, the second deployable joint member being coupled to the second portion of the medical device, the medical device configured to be inserted into a body of a patient.

7. A medical device comprising:
  a first deployable joint member;
  a second deployable joint member; and
  a plurality of flexures coupled to the first deployable joint member and the second deployable joint member,
  the first deployable joint member, the second deployable joint member, and the plurality of flexures being integrally formed from a single, planar sheet of material, the medical device configured to move from a compact state to a deployed state, the compact state being a state in which the first deployable joint member is substantially flat, the second deployable joint member is substantially flat, and the first deployable joint member, the second deployable joint member, and the plurality of flexures are stacked on top of each other, the deployed state being a state in which the first deployable joint member forms a first convex surface portion and the second deployable joint member forms a second convex surface portion.

8. The medical device of claim 7, wherein the first deployable joint member includes a first curved crease forming a first foldable portion, and a second curved crease forming a second foldable portion, the first foldable portion and the second foldable portion being configured to move toward each other to form the first convex surface portion.

9. The medical device of claim 8, wherein the first deployable joint member includes a first lateral side and a second lateral side, the first deployable joint member including a first end and a second end, the first curved crease extending from an intersection of the first lateral side and the first end to an intersection of the second lateral side and the first end, the second curved crease extending from an intersection of the first lateral side and the second end to an intersection of the second lateral side and the second end.

10. The medical device of claim 9, wherein the first end includes a curved portion, and the first curved crease having a curvature larger than a curvature of the curved portion of the first end.

11. The medical device of claim 10, wherein the plurality of flexures include a first flexure, a second flexure, and a third flexure.

12. The medical device of claim 11, wherein the first flexure and the second flexure extend from the first lateral side of the first deployable joint member, and the third flexure extends from the second lateral side of the first deployable joint member.

13. The medical device of claim 7,
in response to the medical device being in the deployed state, the first convex surface portion is configured to roll with respect the second convex surface portion.

14. A medical device comprising:
a deployable rolling joint including:
a first deployable joint member having a first curved crease forming a first foldable portion, and a second curved crease forming a second foldable portion, the first curved crease extending from a first corner of the first deployable joint member to a second corner of the first deployable joint member;
a second deployable joint member having a first curved crease forming a first foldable portion, and a second curved crease forming a second foldable portion, the first curved crease of the second deployable joint member extending from a first corner of the second deployable joint member to a second corner of the second deployable joint member; and
a plurality of flexures coupled to the first deployable joint member and the second deployable joint member,
the deployable rolling joint configured to move from a compact state to a deployed state by moving the first foldable portion of the first deployable joint member and the second foldable portion of the first deployable joint member toward each other, and moving the first foldable portion of the second deployable joint member and the second foldable portion of the second deployable joint member toward each other.

15. The medical device of claim 14, wherein the first deployable joint member, the second deployable joint member, and the plurality of flexures are integrally formed from a single, planar sheet of material.

16. The medical device of claim 14, wherein the first deployable joint member includes a first lateral side, a second lateral side, a first end, and a second end, wherein the first corner of the first deployable joint member is defined by an intersection of the first lateral side and the first end, and the second corner of the first deployable joint member is defined by an intersection of the second lateral side and the first end.

17. The medical device of claim 16, wherein the first curved crease has a curvature larger than a curvature of the first end.

18. The medical device of claim 14, wherein the second curved crease of the first deployable joint member extends from a third corner of the first deployable joint member to a fourth corner of the first deployable joint member.

19. The medical device of claim 14, wherein, in the deployed state, the first deployable joint member forms a convex surface portion and the second deployable joint member forms a convex surface portion.

20. The medical device of claim 14, wherein, in the compact state, the first deployable joint member is substantially flat, the second deployable joint member is substantially flat, and the first deployable joint member, the second deployable joint member, and the plurality of flexures are stacked on top of each other.

* * * * *

UNITED STATES PATENT AND TRADEMARK OFFICE
CERTIFICATE OF CORRECTION

PATENT NO. : 10,227,804 B2
APPLICATION NO. : 14/969979
DATED : March 12, 2019
INVENTOR(S) : Howell et al.

Page 1 of 1

It is certified that error appears in the above-identified patent and that said Letters Patent is hereby corrected as shown below:

In the Claims

In Column 26, Claim 4, Line 43, delete "firming" and insert -- forming --, therefor.

Signed and Sealed this
Third Day of September, 2019

Andrei Iancu
*Director of the United States Patent and Trademark Office*